United States Patent
Zhang et al.

(10) Patent No.: US 11,154,479 B1
(45) Date of Patent: *Oct. 26, 2021

(54) METHODS OF REMOVING COLOR FROM COLOR-TREATED HAIR

(71) Applicant: L'Oreal, Paris (FR)

(72) Inventors: Guojin Zhang, Westfield, NJ (US); Ronak Rughani, Edison, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/888,821

(22) Filed: May 31, 2020

(51) Int. Cl.
*A61Q 5/10* (2006.01)
*A61K 8/49* (2006.01)
*A61K 8/60* (2006.01)
*A61K 8/41* (2006.01)

(52) U.S. Cl.
CPC ............ *A61K 8/4946* (2013.01); *A61K 8/416* (2013.01); *A61K 8/604* (2013.01); *A61K 2800/10* (2013.01)

(58) Field of Classification Search
CPC .......... A61Q 5/065; A61K 8/494; A61K 8/49; A61K 8/4946; A61K 8/416; A61K 8/463; A61K 8/4913; A61K 2800/5426
USPC ............................................................ 8/431
See application file for complete search history.

(56) References Cited

U.S. PATENT DOCUMENTS

| | | | |
|---|---|---|---|
| 3,666,403 A | 5/1972 | Shimauchi et al. | |
| 5,651,960 A | 7/1997 | Chan et al. | |
| 6,171,347 B1 | 1/2001 | Kunz et al. | |
| 7,208,019 B2 | 4/2007 | Lalleman et al. | |
| 7,776,806 B2 | 8/2010 | Tokunaga | |
| 8,071,080 B2 | 12/2011 | Giroud | |
| 2004/0005286 A1 | 1/2004 | Giroud | |
| 2005/0144739 A1 | 7/2005 | Lalleman et al. | |
| 2006/0070191 A1 | 4/2006 | Lang et al. | |
| 2006/0100114 A1 | 5/2006 | Molenda et al. | |
| 2007/0124872 A1* | 6/2007 | Eliu | A61K 8/4926 8/406 |
| 2011/0256081 A1 | 10/2011 | Hawkes et al. | |
| 2015/0328116 A1 | 11/2015 | Patel et al. | |
| 2015/0335548 A1 | 11/2015 | Patel et al. | |
| 2016/0177222 A1 | 6/2016 | Bianchetti et al. | |
| 2016/0367462 A1* | 12/2016 | Samain | A61K 8/4946 |

FOREIGN PATENT DOCUMENTS

| | | |
|---|---|---|
| CN | 106420610 A | 2/2017 |
| DE | 10-2005-026355 A1 | 12/2006 |
| DE | 10-2005-032798 A1 | 1/2007 |
| DE | 10-2005-056155 A1 | 5/2007 |
| EP | 0714954 A2 | 6/1996 |

(Continued)

OTHER PUBLICATIONS

Porter, M.R., "Handbook of Surfactants," published by Blackie & Son (Glasgow and London), 1991, pp. 116-178.

(Continued)

*Primary Examiner* — Eisa B Elhilo
(74) *Attorney, Agent, or Firm* — The Marbury Law Group, PLLC

(57) ABSTRACT

The disclosure relates to compositions and methods for removing direct dyes from hair, the methods comprising contacting hair with a composition comprising at least one organic salt selected from imidazolium-based compounds and/or ammonium-based compounds.

22 Claims, 3 Drawing Sheets

(56) References Cited

FOREIGN PATENT DOCUMENTS

| | | | |
|---|---|---|---|
| FR | 2935266 | A1 | 3/2010 |
| FR | 2971153 | A1 | 8/2012 |
| FR | 2971155 | A1 | 8/2012 |
| KR | 2003-0084158 | A | 11/2003 |
| KR | 10-2011-0057647 | A | 6/2011 |
| WO | 95/01772 | A1 | 1/1995 |
| WO | 95/15144 | A1 | 6/1995 |
| WO | 1998/023247 | A1 | 6/1998 |
| WO | 2007/059822 | A1 | 5/2007 |
| WO | 2013/024099 | A1 | 2/2013 |
| WO | 2013/079528 | A1 | 6/2013 |
| WO | 2014/123805 | A1 | 8/2014 |
| WO | 2018/065827 | A1 | 4/2018 |
| WO | 2020/132182 | A1 | 6/2020 |

OTHER PUBLICATIONS

Copending U.S. Appl. No. 16/715,034, filed Dec. 16, 2019 (now abandoned).
Copending U.S. Appl. No. 16/715,079, filed Dec. 16, 2019.
Copending U.S. Appl. No. 16/716,266, filed Dec. 16, 2019 (now abandoned).
Chen, Jingyu et al., "What Happens During Natural Protein Fibre Dissolution in Ionic Liquids," Materials, vol. 7, No. 9, Aug. 28, 2014, pp. 6158-6168.
Meksi, Nizar et al., "A review of progress in the ecological application of ionic liquids in textile processes," Journal of Cleaner Production, vol. 161, May 16, 2017, pp. 105-126.
Parnian, Jafari-Chashmi et al., "The Strong Synergistic Interaction Between Surface Active Ionic Liquid and Anionic Surfactant in the Mixed Micelle Using the Spectrophotometric Method," Journal of Molecular Liquids, vol. 269, Aug. 23, 2018, pp. 816-823.
International Search Report and Written Opinion for counterpart Application No. PCT/US2019/067371, dated Apr. 7, 2020.
International Search Report and Written Opinion for counterpart Application No. PCT/US2019/067375, dated Mar. 23, 2020.
Yuan, Jiugang et al., "Enhancing Dye Adsorption of Wool Fibers with 1-butyl-3-methylimidozolium Chloride Ionic Liquid Processing," Textile Research Journal, vol. 80, No. 18, Jun. 30, 2010, pp. 1898-1904.
International Search Report and Written Opinion for counterpart Application No. PCT/US2019/067373, dated Mar. 23, 2020.
Non-Final Office Action for copending U.S. Appl. No. 16/399,353, dated Apr. 30, 2020.
Copending U.S. Appl. No. 16/888,835, filed May 31, 2020.
Non-Final Office Action for copending U.S. Appl. No. 16/715,079, dated Nov. 4, 2020.
STIC Search report dated Aug. 26, 2020.
Non-Final Office Action for copending U.S. Appl. No. 16/888,835, dated Nov. 6, 2020.
Final Office Action for copending U.S. Appl. No. 16/399,353, dated Oct. 16, 2020.
Copending U.S. Appl. No. 16/399,353, filed Dec. 16, 2019.
International Search Report and Written Opinion for counterpart Application No. PCT/US2020/030115, dated Jul. 30, 2020.
Final Office Action for copending U.S. Appl. No. 16/888,835, dated Mar. 16, 2021.
Final Office Action for copending U.S. Appl. No. 16/715,079, dated Mar. 3, 2021.
Non-Final Office Action for copending U.S. Appl. No. 16/399,353, dated Jun. 24, 2021.
International Preliminary Report on Patentability for counterpart Application No. PCT/US2019/067371, dated Jul. 1, 2021.

\* cited by examiner

METHODS OF REMOVING COLOR FROM COLOR-TREATED HAIR

FIELD OF THE DISCLOSURE

The present disclosure generally relates to compositions for use in removing color from color-treated or pre-dyed hair and methods of removing color from color-treated or pre-dyed hair, and more particularly using organic salts to remove direct dyes from color-treated or pre-dyed hair.

BACKGROUND

The process of changing the color of hair can involve depositing an artificial color onto the hair which provides a different shade or color to the hair, and/or lifting the color of the hair, such as lightening the color of dark hair to lighter shades.

Imparting a color change or color effect on hair can be done using permanent, semi-permanent, or temporary hair coloring products. Semi-permanent dyeing uses direct dyes, which are nonionic or ionic dyes and colored compounds capable of producing a more or less pronounced change of the natural color of the hair. These dyes may or may not be used in the presence of an oxidizing agent. In contrast with oxidation dye precursors, a direct dye is a relatively large molecule that does not penetrate easily into the core of the fiber. Nevertheless, such dyes can be resistant to shampoo-washing, even after several washes.

However, many consumers desire to quickly change hair color. That is, they wish to dye the hair a particular color and then change to another color before the first color has naturally washed out, and thus must use a color removal product. Most color removal products in the current cosmetic market are based on destroying dyes placed in or on the hair by means of oxidative or reductive reactions. However, those approaches have significant drawbacks of damaging hair fibers. Thus, there is a desire to provide ways to accelerate the removal of direct dyes from color-treated hair, and particularly without damaging the hair.

SUMMARY OF THE DISCLOSURE

One aspect of the disclosure pertains to a method of removing one or more direct dye(s) from hair. In one or more embodiments, the method comprises:

a. contacting hair with a composition comprising:

i. an organic salt selected from:

an imidazolium-based compound having a structure represented by Formula (I) below:

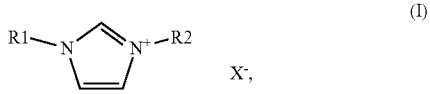

(I)

wherein R1 and R2 are each independently a linear or branched alkyl group having 1-16 carbon atoms, and $X^-$ is selected from halides, carboxylates, $C_{1-16}$ fatty acid carboxylates, phosphates, phosphate derivatives, tosylates, tosylate derivatives, sulfates or sulfate derivatives, an ammonium-based compound having a structure represented by Formula (II) below:

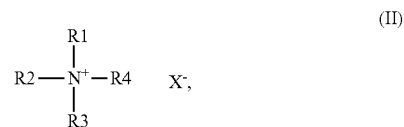

(II)

wherein R1, R2, R3 and R4 are each independently a saturated or unsaturated, linear, branched or cyclic group with a carbon chain length of $C_{1-20}$, and optionally substituted by one or more hydroxyl, amino $C_{1-4}$ radicals, alkylamino, carboxy, carboxylate, carbamide, $C_{1-4}$ alkoxy, $-SO_3H$, sulfonate or aryl, and $X^-$ is selected from halides, carboxylates, $C_{1-16}$ fatty acid carboxylates, phosphates, phosphate derivatives, tosylates, tosylate derivatives, sulfates or sulfate derivatives, and a combination thereof; and b. rinsing the composition from the hair.

Another aspect of the disclosure pertains to a method of removing color from or controlling the removal of color from or lightening the color of hair, the method comprising:

a. contacting hair with a composition comprising the organic salt of the present disclosure; and b. rinsing the composition from the hair;

wherein the hair has been pre-dyed with one or more direct dye(s).

Another aspect of the disclosure relates to the use of organic salts and to compositions containing organic salts, the salts being selected from the above-described imidazolium-based compounds and/or ammonium-based compounds in order to remove the one or more direct dyes from color-treated hair or hair pre-dyed with the one or more direct dye(s).

In various embodiments, the hair has been pre-dyed with one or more direct dye(s) having a positive Log $P_{ow}$ value, such as a hydrophobic direct dye, or one or more direct dye(s) having a negative Log $P_{ow}$ value, such as a cationic direct dye, or one or more direct dye(s) having a neutral Log $P_{ow}$ value, such as a nonionic direct dye, or combinations thereof.

DETAILED DESCRIPTION OF THE DISCLOSURE

Figure 1:
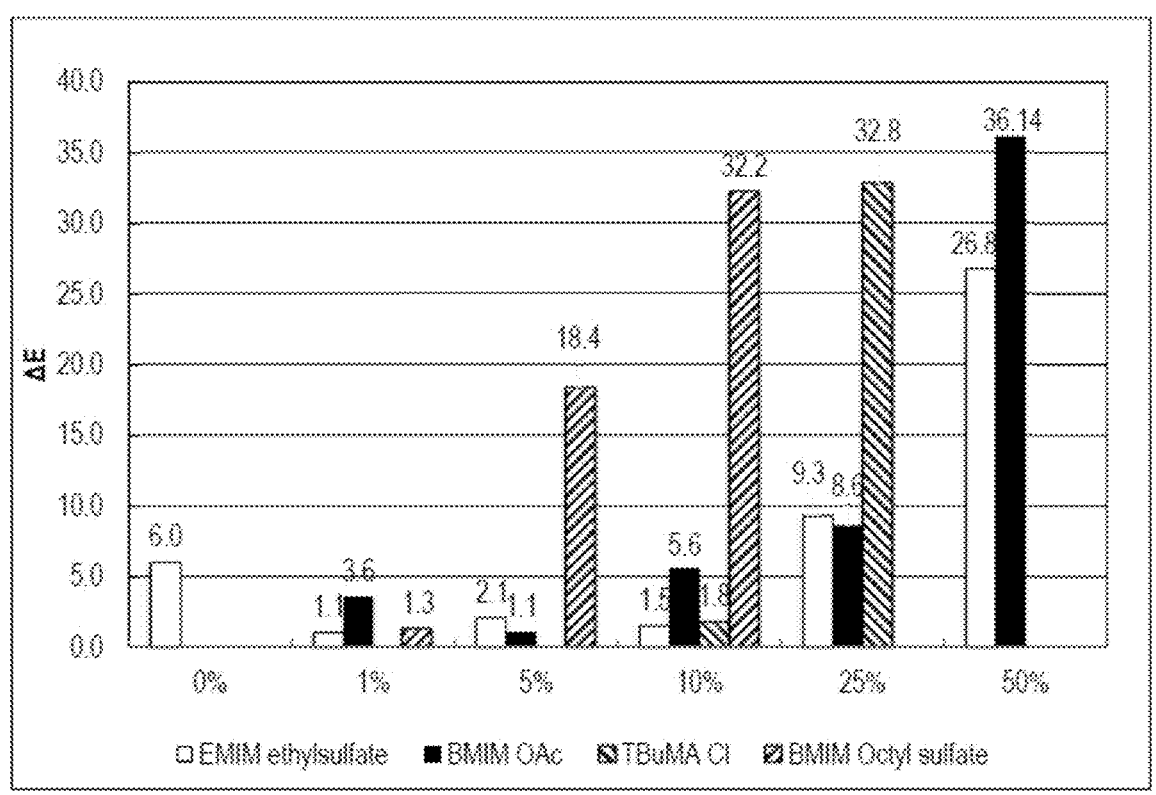
FIG. 1 is a graphical representation of ΔE values of several dyed hair swatches treated with solutions containing various concentrations of organic salts and evaluated for dye removal, as well as a control.

The present disclosure relates to a method of removing one or more direct dye(s) from hair. In one or more embodiments, the method comprises:

a. contacting hair with a composition comprising:

i. an organic salt selected from:

an imidazolium-based compound having a structure represented by Formula (I) below:

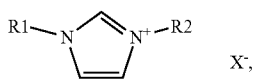

(I)

wherein R1 and R2 are each independently a linear or branched alkyl group having 1-16 carbon atoms, and $X^-$ is selected from halides, carboxylates, $C_{1-6}$ fatty acid carboxylates, phosphates, phosphate derivatives, tosylates, tosylate derivatives, sulfates or sulfate derivatives, an ammonium-based compound having a structure represented by Formula (II) below:

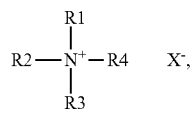

(II)

wherein R1, R2, R3 and R4 are each independently a saturated or unsaturated, linear, branched or cyclic group with a carbon chain length of $C_{1-20}$, and optionally substituted by one or more hydroxyl, amino $C_{1-4}$ radicals, alkylamino, carboxy, carboxylate, carbamide, $C_{1-4}$ alkoxy, $-SO_3H$, sulfonate or aryl, and $X^-$ is selected from halides, carboxylates, $C_{1-16}$ fatty acid carboxylates, phosphates, phosphate derivatives, tosylates, tosylate derivatives, sulfates or sulfate derivatives, and a combination thereof; and b. rinsing the composition from the hair.

In some embodiments, R1, R2, R3 and R4 of the imidazolium-based compound having a structure represented by Formula (I) are each independently a linear or branched alkyl group with a carbon chain length of $C_{1-20}$, and $X^-$ of Formula (I) is selected from carboxylates, $C_{1-16}$ fatty acid carboxylates, sulfates, or sulfate derivatives, including alkyl sulfates.

In some embodiments, the organic salt comprises an imidazolium-based compound selected from butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, and combinations thereof.

In some embodiments, the ammonium-based compound of Formula (II) is selected from:

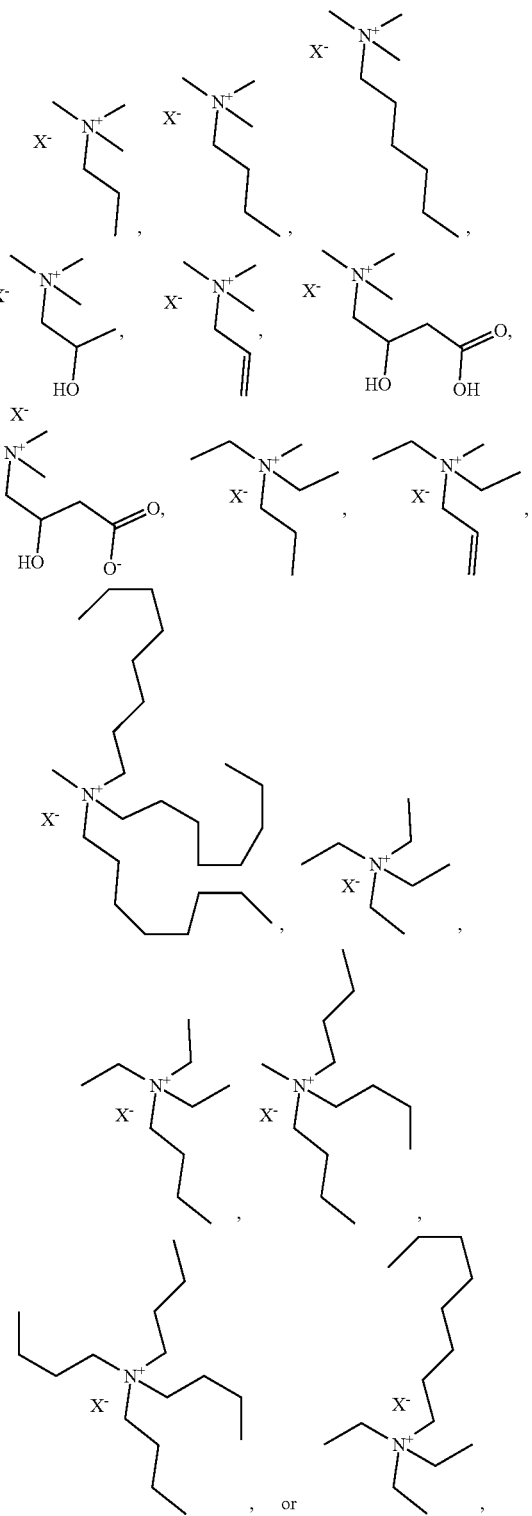

wherein $X^-$ of Formula (II) is selected from halides, carboxylates, $C_{1-16}$ fatty acid carboxylates, phosphates, phosphate derivatives, tosylates, tosylate derivatives, sulfates or sulfate derivatives.

In an embodiment, the organic salt comprises an ammonium-based compound comprising a tributylmethyl ammonium salt, such as tributylmethyl ammonium chloride.

In an embodiment, the organic salt is selected from butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, tributylmethyl ammonium chloride, or combinations thereof.

In various embodiments, the hair to be contacted with the hair treatment or the hair color removal compositions of the present disclosure has been pre-dyed with one or more direct dye(s) having a positive Log $P_{ow}$ value, or one or more direct dye(s) having a negative Log $P_{ow}$ value, or one or more direct dye(s) having a neutral Log $P_{ow}$ value, or combinations thereof.

In various embodiments, the hair to be contacted with the hair treatment or the hair color removal compositions of the present disclosure has been pre-dyed with one or more direct dye(s) having a positive Log $P_{ow}$ value.

In various embodiments, the hair to be contacted with the hair treatment or the hair color removal compositions of the present disclosure has been pre-dyed with one or more direct dye(s) having a positive Log $P_{ow}$ value including at least one hydrophobic direct dye.

In one or more embodiments, the hydrophobic direct dye is selected from HC blue 15, hydroxyanthraquinoneaminopropyl methyl morpholinium methosulfate, Basic violet 2, Disperse violet 1, Disperse red 15, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylaminophenol, Acid red 33, HC violet no.1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no.7, Acid red 92, Acid violet 43, Ext violet 2, Acid green 25, Acid black 1, and combinations thereof.

In various embodiments, the hair to be contacted with the hair treatment or the hair color removal compositions of the present disclosure has been pre-dyed with one or more direct dye(s) having a negative Log $P_{ow}$ value.

In various embodiments, the hair to be contacted with the hair treatment or the hair color removal compositions of the present disclosure has been pre-dyed with one or more direct dye(s) having a negative Log $P_{ow}$ value including at least one cationic direct dye.

In one or more embodiments, the cationic direct dye is selected from the group consisting of basic orange 31, basic red 51, basic yellow 57, HC blue no.2, Acid yellow 23, Basic orange 31, Basic yellow 87, Acid yellow 3, HC Red 3, Acid blue 9, Basic brown 17, and combinations thereof.

In various embodiments, the hair to be contacted with the hair treatment or the hair color removal compositions of the present disclosure has been pre-dyed with one or more direct dye(s) comprising at least one hydrophobic direct dyes and at least one cationic direct dye.

In some embodiments, the composition of the present disclosure further comprises at least one surfactant.

In some embodiments, the composition of the present disclosure can be combined with another composition containing at least one surfactant such as an anionic surfactant or a non-ionic surfactant. In some cases, the composition of the present disclosure can be combined with a shampoo composition containing an anionic surfactant.

Suitable examples of the surfactant include anionic surfactants such as alkyl(ether) sulfates, alkyl sulfates, alkenyl ether sulfates, alkenyl sulfates, sulfosuccinates, sarcosinates, isethionates, and combinations thereof. For example, the anionic surfactants may be chosen from sodium laureth sulfate, ammonium capryleth sulfate, ammonium pareth-25 sulfate, ammonium myreth sulfate, ammonium laureth sulfate, sodium decyl ether sulfate, sodium lauryl sulfate, sodium dodecyl sulfate, ammonium lauryl sulfate, disodium laureth sulfosuccinate, diethylhexyl sodium sulfosuccinate, dioctyl sodium sulfosuccinate, sodium cocoyl isethionate, sodium methy; isethionate, sodium oleoyl isethionate, sodium lauroyl methyl isethionate, sodium cocoyl methyl isethionate, sodium oleoyl methyl isethionate, sodium N-lauroyl sarcosinate, disodium laureth sulfosuccinate, and combinations thereof.

Other suitable examples of the surfactant include amphoteric surfactants such as alkyl betaines, alkyl amido betaines, alkylampho(di)acetates, alkylamphopropionates, and alkanolamides. Examples of amphoteric surfactants are cocamidopropyl betaine, coco-betaine, Sodium cocoamphopropionate, and combinations thereof.

Suitable examples of the surfactant include nonionic surfactants such as alkylpolyglucosides. Examples of alkylpolyglucosides are decyl glucoside, coco-glucoside, cetearyl glucoside, and lauryl glucoside.

In one or more embodiments, the surfactant comprises anionic surfactants selected from sodium lauryl sulfate, sodium laureth sulfate, sodium dodecyl sulfate, ammonium lauryl sulfate, ammonium laureth sulfate, and combinations thereof.

In one or more embodiments, the surfactant comprises alkylpolyglucosides selected from decyl glucoside, coco-glucoside, lauryl glucoside, cetearyl glucoside, and combinations thereof.

In an embodiment, the composition of the present disclosure is a shampoo composition containing at least one anionic surfactant.

In various embodiments, the one or more direct dye(s) is a direct dye having a positive Log $P_{ow}$ value, or a direct dye having a negative Log $P_{ow}$ value, or a direct dye having a neutral Log $P_{ow}$ value, or combinations thereof.

In an embodiment, the methods of the present disclosure are utilized for accelerating the removal of certain direct dyes, such as hydrophobic direct dyes or dyes having a positive Log $P_{ow}$ value from hair.

In some embodiments, the organic salt is selected from butyl-3-methylimidazolium octyl sulfate, butyl-3-methylimidazolium acetate, ethyl-3-methylimidazolium ethylsulfate, tributylmethyl ammonium chloride, and combinations thereof.

In one or more embodiments, the one or more direct dye(s) used to pre-dye the hair is selected from HC Blue 15, Basic Red 51, hydroxyanthraquinoneaminopropyl methyl morpholinium methosulfate, and combinations thereof.

In an embodiment, the methods of the present disclosure are utilized to control the removal of certain direct dyes from hair, such as to control the speed of removal of certain direct dyes and/or to control the amount of certain direct dyes that are to be removed from hair.

Thus, in an embodiment, the present disclosure pertains to a method of controlling the removal of one or more direct dye(s) from hair, the method comprising:

a. contacting the hair with a composition comprising:

i. an organic salt selected from:

an imidazolium-based compound having a structure represented by Formula (I) below:

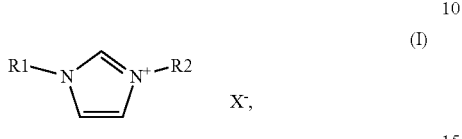

wherein R1 and R2 are each independently a linear or branched alkyl group having 1-16 carbon atoms, and $X^-$ is selected from halides, carboxylates, $C_{1-16}$ fatty acid carboxylates, phosphates, phosphate derivatives, tosylates, tosylate derivatives, sulfates or sulfate derivatives, an ammonium-based compound having a structure represented by Formula (II) below:

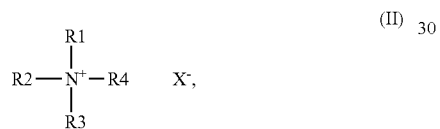

wherein R1, R2, R3 and R4 are each independently a saturated or unsaturated, linear, branched or cyclic group with a carbon chain length of $C_{1-20}$, and optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and $X^-$ is selected from halides, carboxylates, $C_{1-16}$ fatty acid carboxylates, phosphates, phosphate derivatives, tosylates, tosylate derivatives, sulfates or sulfate derivatives, and a combination thereof; and b. rinsing the composition from the hair;

wherein the hair has been pre-dyed with one or more direct dye(s) having a positive Log $P_{ow}$ value, or a direct dye having a negative Log $P_{ow}$ value, or a direct dye having a neutral Log $P_{ow}$ value, or combinations thereof.

In an embodiment, the method of controlling the removal of one or more direct dyes from hair includes the method of accelerating the removal of said direct dyes from hair.

In some embodiments, the organic salt is selected from butyl-3-methylimidazolium octyl sulfate, butyl-3-methylimidazolium acetate, ethyl-3-methylimidazolium ethylsulfate, tributylmethyl ammonium chloride, and combinations thereof. In one or more embodiments, the one or more direct dye(s) used to pre-dye the hair is selected from HC Blue 15, Basic Red 51, hydroxyanthraquinoneaminopropyl methyl morpholinium methosulfate, and combinations thereof.

Another aspect of the disclosure pertains to a method of removing a hydrophobic direct dye from hair, the method comprising:

a. contacting the hair with a composition comprising:

i. an organic salt selected from:

1. an imidazolium-based compound having a structure represented by Formula (I) below:

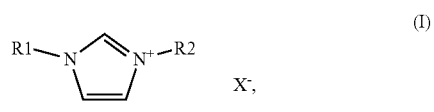

wherein:

R1 and R2 are each independently a linear or branched alkyl groups having 1-16 carbon atoms, and X– is selected from halides, carboxylates, $C_{1-16}$ fatty acid carboxylates, phosphate, phosphate derivatives, tosylate, tosylate derivatives, sulfate and sulfate derivatives;

2. an ammonium-based compound having a structure represented by Formula (II) below:

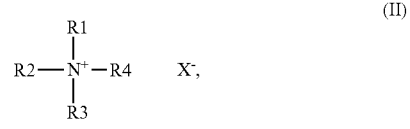

wherein R1, R2, R3 and R4 are each independently selected from linear and branched alkyl groups with the carbon chain length of $C_{1-20}$; and X– is selected from halides, carboxylates, $C_{1-16}$ fatty acid carboxylates, phosphate, phosphate derivatives, tosylate, tosylate derivatives, sulfate and sulfate derivatives; and 3. a combination thereof; and b. rinsing the composition from hair.

Another aspect of the disclosure pertains to a method of removing a cationic direct dye from hair, the method comprising:

a. contacting the hair with a composition comprising:

i. an organic salt selected from:

1. an imidazolium-based compound having a structure represented by Formula (I) below:

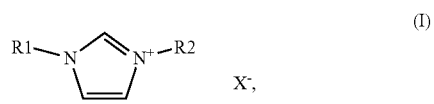

wherein R1 and R2 are each independently a linear or branched alkyl groups having 1-16 carbon atoms, and X– is selected from halides, carboxylates, $C_{1-16}$ fatty acid carboxylates, phosphate derivatives, tosylate, tosylate derivatives, sulfate and sulfate derivatives;

2. an ammonium-based compound having a structure represented by Formula (II) below:

$$R2-\underset{R3}{\overset{R1}{\underset{|}{N^+}}}-R4 \quad X^-, \quad (II)$$

wherein R1, R2, R3 and R4 are each independently selected from linear and branched alkyl groups with the carbon chain length of $C_{1-20}$; and X– is selected from halides, carboxylates, $C_{1-16}$ fatty acid carboxylates, phosphate, phosphate derivatives, tosylate, tosylate derivatives, sulfate and sulfate derivatives; or 3. a combination thereof; and
b. rinsing the composition from hair.

In an embodiment, the imidazolium-based compound and/or ammonium-based compound is present at a concentration of greater than 1 wt. % or ranging from greater than 1 to about 50 wt. %, or from about 1 to about 30 wt. %, or from about 2 to about 25 wt. %, or from about 3 to about 20 wt. %, or from about 3 to about 15 wt. %, or from about 3 to about 10 wt. %, based on the total weight of the composition.

In an embodiment, the organic salt comprises an imidazolium-based compound selected from the group consisting of butyl-3-methylimidazolium octyl sulfate, butyl-3-methylimidazolium acetate, ethyl-3-methylimidazolium ethylsulfate, tributylmethyl ammonium chloride, and combinations thereof.

In some embodiments, the one or more direct dye(s) comprises a direct dye selected from HC Blue 15, hydroxyanthraquinoneaminopropyl methyl morpholinium methosulfate, Basic Red 51, and combinations thereof.

Another aspect of the present disclosure pertains to a method of removing the color from or accelerating the removal of color from or lightening the color of hair, the method comprising:
a. contacting the hair with a composition comprising:
  i. an organic salt selected from:
    1. an imidazolium-based compound selected from butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, and combinations thereof, and preferably selected from butyl-3-methylimidazolium octyl sulfate;
    2. an ammonium-based compound comprising tributylmethyl ammonium salt(s); and
    3. a combination thereof; and
b. rinsing the composition from hair;
wherein the imidazolium-based compound or ammonium-based compound is present at a concentration ranging from greater than 1 to about 50 wt. %, preferably from about 5 to about 30 wt. %, based on the total weight of the composition; and
wherein the hair has been pre-dyed with one or more direct dye(s) selected from hydrophobic direct dyes, cationic direct dyes, nonionic direct dyes, and combinations thereof.

In an embodiment, the hydrophobic direct dye is selected from HC blue 15, hydroxyanthraquinoneaminopropyl methyl morpholinium methosulfate, and combinations thereof.

In an embodiment, the cationic direct dye is selected from basic red 51.

In an embodiment, an amount of the one or more direct dye(s) selected from hydrophobic direct dyes is removed from the hair, thereby resulting in color removal or lightening of the color of the hair.

In an embodiment, an amount of the one or more direct dye(s) selected from cationic direct dyes is removed from the hair, thereby resulting in color removal or lightening of the color of the hair.

In one embodiment, the method of the present disclosure involves removing HC blue 15 and/or hydroxyanthraquinoneaminopropyl methyl morpholinium methosulfate and/or basic red 51 from hair, the method comprising:
a. applying onto the hair or contacting the hair with a composition containing an organic salt selected from an imidazolium-based compound including butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, and combinations thereof, or an ammonium-based compound including tributylmethyl ammonium chloride, or combinations thereof; and
b. rinsing the composition from the hair.

In various embodiments, the method of the present disclosure includes a step of leaving the compositions for removing direct dyes on the hair for a period of time ranging from about 5 to about 60 minutes.

In various embodiments, the treated hair is heated at a temperature ranging from about 25° C. to about 60° C.

In various embodiments, the compositions of the present disclosure can be in the form of a spray, gel, cream, lotion, serum, aqueous solution.

In various embodiments, the compositions of the present disclosure can be a shampoo, rinse-off conditioner, or a rinse-off mask treatment.

In an embodiment, the present disclosure pertains to a hair treatment agent for removing or controlling the removal of one or more direct dye(s) from hair, wherein the agent comprises:
i. a first composition containing an organic salt selected from:
an imidazolium-based compound having a structure represented by Formula (I) below:

$$R1-N\overset{\frown}{\underset{\smile}{\phantom{X}}}N^+-R2 \quad X^-, \quad (I)$$

wherein R1 and R2 are each independently a linear or branched alkyl group having 16 carbon atoms, and X⁻ is selected from halides, carboxylates, $C_{1-16}$ fatty acid carboxylates, phosphates, phosphate derivatives, tosylates, tosylate derivatives, sulfates or sulfate derivatives,
an ammonium-based compound having a structure represented by Formula (II) below:

$$R2-\underset{R3}{\overset{R1}{\underset{|}{N^+}}}-R4 \quad X^-, \quad (II)$$

wherein R1, R2, R3 and R4 are each independently a saturated or unsaturated, linear, branched or cyclic group with a carbon chain length of $C_{1-20}$, and optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and $X^-$ is selected from halides, carboxylates, $C_{1-16}$ fatty acid carboxylates, phosphates, phosphate derivatives, tosylates, tosylate derivatives, sulfates or sulfate derivatives, or a combination thereof; and ii. a second composition containing a surfactant selected from anionic surfactants, amphoteric surfactants, nonionic surfactants, and combinations thereof;

wherein the first and second compositions are combined to form the hair treatment agent or the first and second compositions are applied in a sequential manner or a layering manner onto hair in any order.

In an embodiment, the present disclosure pertains to a kit containing the above described first and second compositions in separate components.

In an embodiment, the second composition is a shampoo.

In an embodiment, the composition for removing color or for lightening the color of hair pre-dyed with one or more direct dye(s) in accordance with the present disclosure comprises an organic salt selected from:

an imidazolium-based compound having a structure represented by Formula (I) below:

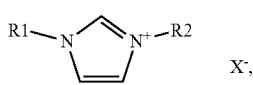

(I)

wherein R1 and R2 are each independently a linear or branched alkyl group having 16 carbon atoms, and $X^-$ is selected from halides, carboxylates, $C_{1-16}$ fatty acid carboxylates, phosphates, phosphate derivatives, tosylates, tosylate derivatives, sulfates or sulfate derivatives, an ammonium-based compound having a structure represented by Formula (II) below:

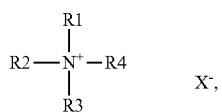

(II)

wherein R1, R2, R3 and R4 are each independently a saturated or unsaturated, linear, branched or cyclic group with a carbon chain length of $C_{1-20}$, and optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and $X^-$ is selected from halides, carboxylates, $C_{1-16}$ fatty acid carboxylates, phosphates, phosphate derivatives, tosylates, tosylate derivatives, sulfates or sulfate derivatives, and a combination thereof;

wherein the imidazolium-based compound and/or the ammonium-based compound is in ionic liquid form.

As used herein, the term "pre-dyed with one or more direct dye(s)" means the hair has been dyed with one or more direct dye(s) prior to contact with the organic salt or composition containing the organic salt.

As used herein, the term "ionic liquid" refers to the organic salt of the present disclosure being in the liquid state or having a melting point of equal to or under 150° C. (preferably 100° C. or preferably less than 100° C.), or in some embodiments, at room temperature. Preferably, the salt remains liquid up to 300 degrees centigrade, and more preferably the salt is liquid at room temperature, that is to say, at a melting point of less than or equal to 50 degrees centigrade and greater than 0 degrees centigrade.

The melting point is measured by differential calorimetric analysis, with a temperature increase rate of 10 degrees centigrade/minute, the melting point then being at a temperature corresponding to the top of the endothermic melting peak obtained during the measurement.

According to the disclosure, the term "hydrophobic ionic liquid" means an ionic liquid having a solubility in water at room temperature (25 degrees centigrade) of less than 5 percent, preferably less than 1 percent by weight, or even less than 0.5 percent. Within the context of the disclosure, the hydrophobic character of the ionic liquid is such that there is phase separation in water.

Within the context of the disclosure, the term "water-soluble" means an organic salt or an ionic liquid which has a solubility in water at 25 degrees centigrade of greater than 1 percent, preferably greater than 5 percent, more preferably greater than 10 percent; that is to say, which forms at this concentration a macroscopically homogeneous, transparent and isotropic medium.

As used herein, the term "contacting" means that the composition comes into contact with the hair so that the composition is exposed to the surfaces of the hair which would normally accommodate direct dye molecules or is exposed to the direct dye molecules on the hair. It can also mean that the composition is applied onto the hair. In some embodiments, this means the hair can be soaked in the composition comprising organic salt, or the composition is applied onto the hair by using the hands or an applicator, or the hair may be mechanically manipulated with the composition (e.g. using hands to manipulate hair in the presence of the composition containing organic salt).

As used herein, the term "rinsing the hair" or "rinsing the composition from the hair" means rinsing or washing the hair with water, or shampooing the hair first, then rinsing the hair with water.

It has been surprisingly discovered that such organic salts are able to greatly accelerate and/or control the removal of direct dyes from color-treated hair. While not wishing to be bound to any particular theory, it is believed that the organic salts are able to physically extract the direct dyes which reside on the surface of hair fibers, as such dye molecules interact with hair protein by non-covalent bonds. It is also believed that the physical extraction of the dyes presents a mild approach to treating hair or removing dyes from dyed hair without introducing harsh chemicals or chemical reactions on hair that can damage or negatively impact the integrity or quality of hair fibers. It is also thought that the organic salts have a high swelling ability in hair fibers.

It has further been discovered that this acceleration can be further enhanced by also including a surfactant in the process, particularly for dyes which have a positive Log $P_{ow}$ value and/or are hydrophobic. While not wishing to be bound by any particular theory, it is thought the surfactants and organic salts form binary surfactant systems and further enhance color removal by increasing both hair wettability and dye solubility, and interact with the dyes by ionic or hydrophobic interaction.

Compositions

Organic Salt

The compositions comprise at least one organic salt. The organic salt of the present disclosure can comprise an organic cation and an inorganic anionic or an inorganic cation and an organic anion or an organic cation and an organic anion.

In an embodiment, the organic salt of the present disclosure comprises an imidazolium-based compound.

In an embodiment, the organic salt of the present disclosure comprises an ammonium-based compound.

In an embodiment, the organic salt of the present disclosure comprises an imidazolium-based compound and an ammonium-based compound.

Imidazolium-Based Compounds

According to one or more embodiments, the organic salt comprises an imidazolium-based compound having a structure represented by Formula (I) below:

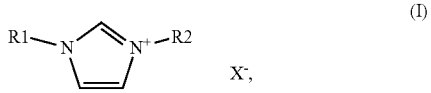

wherein R1 and R2 are each independently selected from linear and branched alkyl groups having 1-16 carbon atoms, and $X^-$ is selected from halides, carboxylates, $C_{1-16}$ fatty acid carboxylates, phosphate, phosphate derivatives, tosylate, tosylate derivatives, sulfate and sulfate derivatives.

In one or more embodiments, each R group is each independently selected from methyl, ethyl, propyl or butyl. In some embodiments, R2 is methyl, ethyl, propyl, or butyl and R1 is methyl, ethyl, propyl, or butyl, in any combination. Examples include butyl-3-methylimidazolium, butyl-3-methylimidazolium, ethyl-3-methylimidazolium, 1,3-ethyl imidazolium.

In some embodiments, $X^-$ comprises a halide. In further embodiments, the halide comprises $F^-$, $Br^-$, $Cl^-$, or $I^-$. In one or more embodiments, $X^-$ comprises a phosphate, phosphate derivatives, tosylate, tosylate derivatives, sulfate and sulfate derivatives. Such phosphate, tosylate and sulfate derivatives may include alkyl phosphates, alkyl tosylates and alkyl sulfates, respectively. Such phosphate, tosylate and sulfate derivatives may also include halo phosphates, halo tosylates and halo sulfates, respectively. The alkyl groups of such alkyl sulfates could include 1, 2, 3, 4, 5, 6, 7, 8, 9, 10, 11 or 12 carbon atoms. In further embodiments, the alkyl sulfate comprises ethyl sulfate or octyl sulfate. In some embodiments, $X^-$ comprises a carboxylate or fatty acid carboxylate. The fatty acid carboxylate could include 1, 2, 3, 4, 5, 6, 7, 8, 9, 10, 11, 12, 13 or 14 carbon atoms. In further embodiments, the carboxylate comprises acetate.

In some embodiments, the organic salt comprises an imidazolium-based compound selected from the group consisting of butyl-3-methylimidazolium octyl sulfate, butyl-3-methylimidazolium acetate, ethyl-3-methylimidazolium ethylsulfate, 1,3-ethyl imidazolium acetate, and combinations thereof.

Ammonium-Based Compounds

According to one or more embodiments, the organic salt comprises an ammonium-based compound having a structure represented by Formula (II) below:

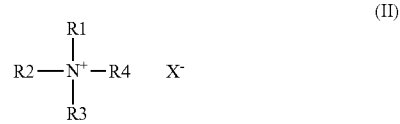

wherein R1, R2, R3 and R4 are each independently selected from saturated or unsaturated, linear, branched or cyclic groups with the carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and $X^-$ is selected from the group consisting of halides, carboxylates, $C_{1-16}$ fatty acid carboxylates, phosphate, phosphate derivatives, tosylate, tosylate derivatives, sulfate and sulfate derivatives.

In some embodiments, R1, R2, R3 and R4 are each independently selected from linear and branched alkyl groups with the carbon chain length of $C_{1-20}$.

In one or more embodiments, R1 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl; R2 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl; R3 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl; and R4 is methyl, ethyl, propyl, butyl, pentyl, hexyl, heptyl, octyl, nonyl, decyl, undecyl, dodecyl, trydecyl, tetradecyl, pentadecyl, hexadecyl, heptadecyl, octadecyl, nonadecyl or eicosyl in any combination.

In one or more embodiments, the ammonium-based compound has a structure selected from the group consisting of:

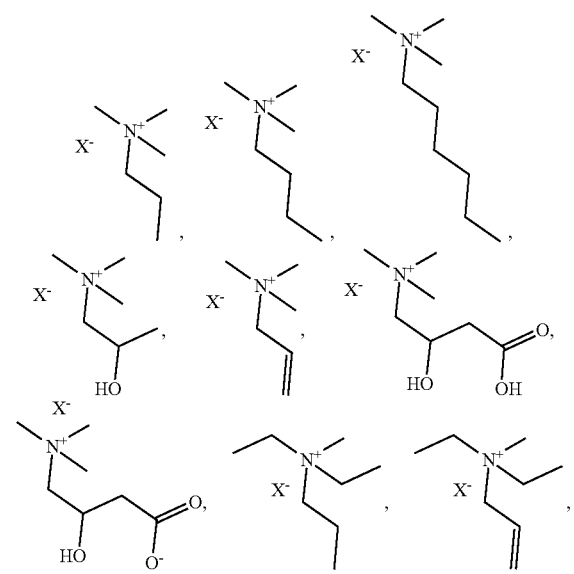

-continued

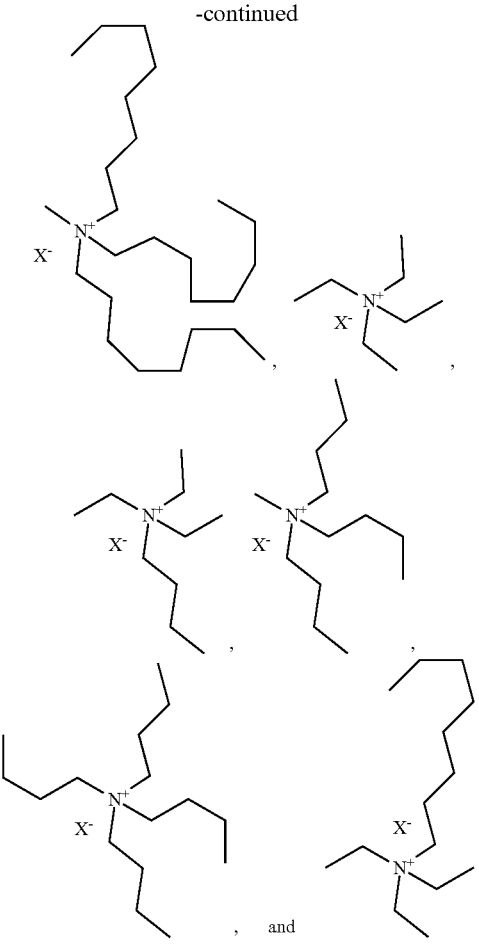

In some embodiments, X⁻ comprises a halide. In further embodiments, the halide comprises F⁻, Br⁻, Cl⁻, or I⁻. In one or more embodiments, X⁻ comprises a phosphate, phosphate derivatives, tosylate, tosylate derivatives, sulfate and sulfate derivatives. Such phosphate, tosylate and sulfate derivatives may include alkyl phosphates, alkyl tosylates and alkyl sulfates, respectively. Such phosphate, tosylate and sulfate derivatives may also include halo phosphates, halo tosylates and halo sulfates, respectively. The alkyl groups of such alkyl sulfates could include 1, 2, 3, 4, 5, 6, 7, 8, 9, 10, 11, 12, 13, 14, 15, or 16 carbon atoms. In further embodiments, the alkyl sulfate comprises ethyl sulfate or octyl sulfate. In some embodiments, X⁻ comprises a carboxylate or fatty acid carboxylate. The fatty acid carboxylate could include 1, 2, 3, 4, 5, 6, 7, 8, 9, 10, 11, 12, 13 or 14 carbon atoms. In further embodiments, the carboxylate comprises acetate.

In some embodiments, the organic salt in the present disclosure comprises an ammonium-based compound including tributylmethyl ammonium chloride (TBuMA Cl).

The organic salt (or salt of an organic molecule) of the present disclosure can be in the form of an ionic liquid. In some embodiments, the ionic liquid can hydrophobic. In some other embodiments, the ionic liquid can be water-soluble.

In one or more embodiments, the organic salt includes an imidazolium-based compound in ionic liquid form.

In one or more embodiments, the organic salt includes an ammonium-based compound in ionic liquid form.

In one or more embodiments, the organic salt includes an imidazolium-based compound and ammonium-based compound in ionic liquid forms.

In one or more embodiments, the organic salt includes an imidazolium-based compound in ionic liquid form and selected from butyl-3-methylimidazolium octyl sulfate, butyl-3-methylimidazolium acetate, ethyl-3-methylimidazolium ethylsulfate, tributylmethyl ammonium chloride, and combinations thereof.

In one or more embodiments, the organic salt comprises an imidazolium-based compound and/or an ammonium-based compound that are not in ionic liquid form or that are in ionic liquid form or that are combinations of salts that are not in ionic liquid form and salts that are in ionic liquid form.

In one or more embodiments, the organic salt is contained in or combined with a solvent such as water or one or more organic solvents or a mixture of water and one or more organic solvents.

In an embodiment, when the organic salt is contained in or combined with a solvent such as water or one or more organic solvents or a mixture of water and one or more organic solvents, the organic salt dissociates into cations and anions in the solvent (i.e., the organic salt is no longer in ionic liquid form).

In an embodiment, when the organic salt comprises an ionic liquid and is contained in or combined with a solvent such as water or one or more organic solvents or a mixture of water and one or more organic solvents, a portion of the organic salt dissociates into cations and anions in the solvent (i.e., the organic salt is no longer in ionic liquid form) and a portion of the organic salt remains an ionic liquid.

In one or more embodiments, the organic salts in the methods and compositions of the present disclosure are advantageously used on hair that has been dyed with direct dyes, in particular, hydrophobic dyes and/or dyes which have a positive Log $P_{ow}$ value, in order to accelerate color removal. Such hydrophobic dyes interact with hair fibers through strong hydrophobic interactions, and are thus difficult to be removed using general washing with water or shampooing with conventional shampoos. In some embodiments, the dyes advantageously removed using organic salts contain an anthraquinone derivative and/or multi-aromatic rings, and have low solubility in water.

In various embodiments, the organic salt may be present in the composition at a concentration ranging from about 0.01, 0.1, 0.2, 0.3, 0.4, 0.5, 1, 2, 3, 4, 5, 6, 7, 8, 9, 10, 11, 12, 13, 14, 15, 16, 17, 19, 20, 25, 30, 35 or 40 to about 15, 16, 17, 19, 20, 25, 30, 35, 40, 45, 50, 55, 60, 65 or 70 wt. % by total weight of the composition. In some embodiments, the organic salt may be present at a concentration ranging from about 1, 2, 3, 4, 5, 6, 7, 8, 9, 10, 11, 12, 13, 14, 15, 16, 17, 19, 20, 25, 30, 35 or 40 to about 15, 16, 17, 19, 20, 25, 30, 35, 40, 45, 50, 55, 60, 65 or 70 wt. % by total weight of the composition. In embodiments when a surfactant is present, the organic salt may be present at a concentration ranging from about 0.01, 0.1, 0.2, 0.3, 0.4, 0.5, 1, 2, 3, 4, 5, 6, 7, 8, 9, 10, 11, 12, 13, 14, 15, 16, 17, 19, 20, 25, 30, 35 or 40 to about 5, 6, 7, 8, 9, 10, 11, 12, 13, 14, 15, 16, 17, 19, 20, 25, 30, 35, 40, 45, 50, 55, 60, 65 or 70 wt. % by total weight of the composition.

In other embodiments, the total amount of the organic salt in the composition of the present disclosure is greater than 1 wt %, based on the total weight of the composition. In some cases, the total amount of the organic salt in the composition ranges from greater than 1 to about 50 wt. %, or from about 2 to about 40 wt. %, or from about 4 to about 35 wt. %, or from about 5 to about 30 wt. %, or from about 5 to about 25 wt. %, or from about 5 to about 20 wt. %, or from about 5 to about 15 wt. %, or from about 5 to about 10 wt. %, or from about 10 to about 50 wt. %, or from about 20 to about 50 wt. %, or from about 25 to about 50 wt. %, based on the total weight of the composition, including ranges and sub-ranges therebetween.

For example, when the organic salt is selected from butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, tributylmethyl ammonium chloride, and combinations thereof, the total amount of the organic salt in the composition may range from greater than 1 to about 50 wt. %, or from about 2 to about 40 wt. %, or from about 4 to about 35 wt. %, or from about 5 to about 30 wt. %, or from about 5 to about 25 wt. %, or from about 5 to about 20 wt. %, or from about 5 to about 15 wt. %, or from about 5 to about 10 wt. %, based on the total weight of the composition, including ranges and sub-ranges therebetween.

As a further example, when the organic salt is selected from butyl-3-methylimidazolium octyl sulfate, butyl-3-methylimidazolium acetate, ethyl-3-methylimidazolium ethylsulfate, 1-ethyl-3-ethyl imidazolium acetate, 1-ethyl-3-methylimidazolium tosylate, tributylmethyl ammonium chloride, and combinations thereof, the total amount of the organic salt in the composition may be about 2, 3, 4, 5, 6, 7, 8, 9, 10, 11, 12, 13, 14, 15, 16, 17, 18, 19, or 20 wt. %, based on the total weight of the composition.

Surfactants

Although not required, in some embodiments surfactants or emulsifiers are used in combination with the organic salts of the present disclosure in order to further accelerate the removal of color from or lighten the color of hair dyed with direct dyes (semi-permanent color). If the surfactant has a very long hydrocarbon chain (i.e., more than 18-20 carbons), other emulsifiers may advantageously be added. In some embodiments, the direct dye used to color hair has a positive Log $P_{ow}$ value and the compositions containing organic salts according to the disclosure preferentially comprise at least one surfactant.

Anionic Surfactant

The term "anionic surfactant" means a surfactant comprising, as ionic or ionizable groups, only anionic groups. A species is termed as being "anionic" when it bears at least one permanent negative charge or when it can be ionized as a negatively charged species, under the conditions of use of the composition (for example the medium or the pH) and not comprising any cationic charge. These anionic groups may be chosen from $-CO_2H$, $-CO_2^-$, $-SO_3H$, $-SO_3^-$, $-OSO_3H$, $-OSO_3^-$, $-H_2PO_3$, $-HPO_3^-$, $-PO_3^{2-}$, $-H_2PO_2$, $=HPO_2$, $-HPO_2^-$, $=PO_2^-$, $=POH$, and $=PO^-$ groups.

The anionic surfactants may be sulfate, sulfonate and/or carboxylic (or carboxylate) surfactants, or mixtures thereof.

Sulfate anionic surfactants comprise at least one sulfate function but do not comprise any carboxylate or sulfonate functions. The sulfate anionic surfactants that may be used comprise at least one sulfate function ($-OSO_3H$ or $-OSO_3$).

They may be chosen from the following compounds: alkyl sulfates, alkyl ether sulfates, alkylamido ether sulfates, alkylaryl polyether sulfates, monoglyceride sulfates; and also the salts of these compounds; the alkyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Preferentially, the sulfate anionic surfactants are chosen, alone or as a mixture, from:
alkyl sulfates, especially of C6-C24 or even C12-C20,
alkyl ether sulfates, especially of C6-C24 or even C12-C20, preferably comprising from 2 to 20 ethylene oxide units;
in particular in the form of alkali metal or alkaline-earth metal, ammonium or amino alcohol salts.

Sulfonate anionic surfactants comprise at least one sulfonate function ($-SO_3H$ or $-SO_3^-$) and may optionally also comprise one or more sulfate functions, but do not comprise any carboxylate functions. The sulfonate anionic surfactants that may be used comprise at least one sulfonate function ($-SO_3H$ or $-SO_3-$).

They may be chosen from the following compounds: alkylsulfonates, alkylamidesulfonates, alkylarylsulfonates, α-olefinsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds; the alkyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Preferentially, the sulfonate anionic surfactants are chosen, alone or as a mixture, from:
C6-C24 and especially C12-C20 alkylsulfosuccinates, especially laurylsulfosuccinates;
C6-C24 and especially C12-C20 alkyl ether sulfosuccinates; and
(C6-C24)acylisethionates and preferably (C12-C18)acylisethionates,
in particular in the form of alkali metal or alkaline-earth metal, ammonium or amino alcohol salts.

Carboxylate anionic surfactants comprise at least one carboxylic or carboxylate function ($-COOH$ or $-COO^-$) and may optionally also comprise one or more sulfate and/or sulfonate functions. The carboxylic anionic surfactants that may be used thus comprise at least one carboxylic or carboxylate function ($-COOH$ or $-COO^-$).

They may be chosen from the following compounds: acylglycinates, acyllactylates, acylsarcosinates, acylglutamates; alkyl-D-galactosideuronic acids, alkyl ether carboxylic acids, alkyl(C6-30 aryl) ether carboxylic acids, alkylamido ether carboxylic acids; and also the salts of these compounds; the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Use may also be made of the C6-C24 alkyl monoesters of polyglycoside-polycarboxylic acids, such as C6-C24 alkyl polyglycoside-citrates, C6-C24 alkyl polyglycoside-tartrates and C6-C24 alkyl polyglycoside-sulfosuccinates, and salts thereof.

Among the above carboxylic surfactants, mention may be made most particularly of polyoxyalkylenated alkyl(amido)

ether carboxylic acids and salts thereof, in particular those comprising from 2 to 50 alkylene oxide and in particular ethylene oxide groups, such as the compounds sold by the company Kao under the name Akypo.

The polyoxyalkylenated alkyl(amido) ether carboxylic acids that may be used are preferably chosen from those of formula (1):

wherein:
$R^1$ represents a linear or branched C6-C24 alkyl or alkenyl radical, an alkyl(C8-C9)phenyl radical, a radical R2CONH—CH2-CH2- with R2 denoting a linear or branched C9-C21 alkyl or alkenyl radical, preferably, R1 is a C8-C20 and preferably C8-C18 alkyl radical, and aryl preferably denotes phenyl, n is an integer or decimal number (average value) ranging from 2 to 24 and preferably from 2 to 10, A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenated alkyl(amido) ether carboxylic acids that are particularly preferred are those of formula (1) in which:
R1 denotes a C12-C14 alkyl, cocoyl, oleyl, nonylphenyl or octylphenyl radical,
A denotes a hydrogen or sodium atom, and
n varies from 2 to 20 and preferably from 2 to 10.

Even more preferentially, use is made of compounds of formula (1) in which R denotes a C12 alkyl radical, A denotes a hydrogen or sodium atom and n ranges from 2 to 10.

Preferentially, the carboxylic anionic surfactants are chosen, alone or as a mixture, from:
  acylglutamates, especially of C6-C24 or even C12-C20, such as stearoylglutamates, and in particular disodium stearoylglutamate;
  acylsarcosinates, especially of C6-C24 or even C12-C20, such as palmitoylsarcosinates, and in particular sodium palmitoylsarcosinate;
  acyllactylates, especially of C12-C28 or even C14-C24, such as behenoyllactylates, and in particular sodium behenoyllactylate;
  C6-C24 and especially C12-C20 acylglycinates;
  (C6-C24)alkyl ether carboxylates and especially (C12-C20)alkyl ether carboxylates;
  polyoxyalkylenated ($C_6$-$C_{24}$)alkyl(amido) ether carboxylic acids, in particular those comprising from 2 to 50 ethylene oxide groups; in particular in the form of alkali metal or alkaline-earth metal, ammonium or amino alcohol salts.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

Preferentially, the anionic surfactants are chosen, alone or as a mixture, from:
  C6-C24 and especially C12-C20 alkyl sulfates;
  C6-C24 and especially C12-C20 alkyl ether sulfates; preferably comprising from 2 to 20 ethylene oxide units;
  C6-C24 and especially C12-C20 alkylsulfosuccinates, especially laurylsulfosuccinates;
  C6-C24 and especially C12-C20 alkyl ether sulfosuccinates;
  (C6-C24)acylisethionates and preferably (C12-C18)acylisethionates;
  C6-C24 and especially C12-C20 acylsarcosinates; especially palmitoylsarcosinates;
  (C6-C24)alkyl ether carboxylates, preferably (C12-C20) alkyl ether carboxylates;
  polyoxyalkylenated (C6-C24)alkyl(amido) ether carboxylic acids and salts thereof, in particular those comprising from 2 to 50 alkylene oxide and in particular ethylene oxide groups;
  C6-C24 and especially C12-C20 acylglutamates;
  C6-C24 and especially C12-C20 acylglycinates;
  in particular in the form of alkali metal or alkaline-earth metal, ammonium or amino alcohol salts.

In particular, ($C_{12}$-$C_{20}$)alkyl sulfates, ($C_{12}$-$C_{20}$)alkyl ether sulfates comprising from 2 to 20 ethylene oxide units, especially in the form of alkali metal, ammonium, amino alcohol and alkaline-earth metal salts, or a mixture of these compounds, may be chosen. In at least one embodiment, sodium lauryl ether sulfate containing 2.2 mol of ethylene oxide is chosen.

In other embodiments, the anionic surfactant is chosen from sodium laureth sulfate, sodium lauryl sulfate, sodium lauroyl methyl isethionate, and mixtures thereof.

Amphoteric or Zwitterionic Surfactant

In one or more embodiments, the surfactant comprises one or more amphoteric surfactants. The amphoteric surfactants that may be used in compositions according to the disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group. Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20) alkylamido(C1-C6)alkylsulfobetaines, and mixtures thereof. Among the optionally quaternized secondary or tertiary aliphatic amine derivatives that may be used, mention may also be made of the products of respective structures (A1) and (A2) below:

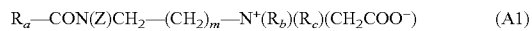

wherein:
$R_a$ represents a $C_{10}$-$C_{30}$ alkyl or alkenyl group derived from an acid $R_a$—COOH preferably present in hydrolysed coconut oil, a heptyl group, a nonyl group or an undecyl group,
$R_b$ represents a β-hydroxyethyl group,
$R_c$ represents a carboxymethyl group;
m is equal to 0, 1 or 2,
Z represents a hydrogen atom or a hydroxyethyl or carboxymethyl group; and

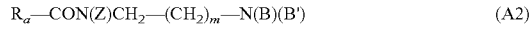

wherein:
B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom,
B' represents —(CH$_2$)$_z$—Y', with z=1 or 2, and Y' representing —COOH, —COOZ', —CH$_2$—CHOH—SO$_3$H or —CH$_2$—CHOH—SO$_3$Z',
m' is equal to 0, 1 or 2,
Z represents a hydrogen atom or a hydroxyethyl or carboxymethyl group,
Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris (hydroxymethyl)aminomethane,
R$_a$' represents a C$_{10}$-C$_{30}$ alkyl or alkenyl group of an acid R$_a$COOH preferably present in hydrolysed linseed oil or coconut oil, an alkyl group, in particular a C$_{17}$ alkyl group, and its iso form, or an unsaturated C$_{17}$ group.

Among the compounds corresponding to formula (A2) in which X' represents a hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

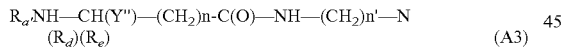

(A3)

wherein:
R$_a$" represents a C$_{10}$-C$_{30}$ alkyl or alkenyl group of an acid R$_a$'—C(O)OH preferably present in hydrolysed linseed oil or coconut oil;
Y" represents the group —C(O)OH, —C(O)OZ", —CH$_2$—CH(OH)—SO$_3$H or the group —CH$_2$—CH(OH)—SO$_3$—Z", with Z" representing a cationic counterion resulting from an alkali metal or alkaline-earth metal, such as sodium, an ammonium ion or an ion resulting from an organic amine;
R$_d$ and R$_e$ represent, independently of each other, a C1-C4 alkyl or hydroxyalkyl radical; and
n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name CHIMEXANE HB.

Preferably, the amphoteric surfactants are chosen from (C8-C20)alkylbetaines, (C8-C20)alkylamido(C1-C6)alkylbetaines, (C8-C20)alkylamphoacetates and (C8-C20)alkylamphodiacetates, and mixtures thereof.

In preferred embodiments of the disclosure, the amphoteric surfactants are chosen from coco-betaine sold by BASF as DEHYTON AB 30.

Non-Ionic Surfactant

Examples of nonionic surfactants that may be used in the composition according to embodiments of the disclosure are described, for example, in the *Handbook of Surfactants* by M. R. Porter, published by Blackie & Son (Glasgow and London), 1991, pp. 116-178. They are especially chosen from alcohols, α-diols and (C$_1$-C$_{20}$) alkylphenols, these compounds being polyethoxylated, polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of alkoxylated alcohols, such as condensates of ethylene oxide and of propylene oxide with fatty alcohols; polyethoxylated fatty amides preferably having from 2 to 30 ethylene oxide units, polyglycerolated fatty amides comprising on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—(C6-24 alkyl)glucamine derivatives, amine oxides such as (C10-14 alkyl) amine oxides or N—(C10-14 acyl)aminopropylmorpholine oxides. Mention may also be made of PEG-40 hydrogenated castor oil.

Mention may also be made of nonionic surfactants of alkyl(poly)glycoside type (also called "alkylpolyglucoside") represented especially by the following general formula:

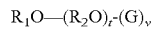

wherein:
R$_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
R2 represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

Preferably, the alkylpolyglycoside surfactants are compounds of the formula described above in which:
R$_1$ denotes a linear or branched, saturated or unsaturated alkyl radical comprising from 8 to 18 carbon atoms,
R$_2$ represents an alkylene radical comprising 2 to 4 carbon atoms,
t denotes a value ranging from 0 to 3 and preferably equal to 0,
G denotes glucose, fructose or galactose, preferably glucose;
the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glycosides 1,4, and especially decyl glucosides and caprylyl/capryl glucosides, are most particularly preferred.

Among the commercial products, mention may be made of the products sold by the company BASF under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glycosides-1,4, especially as an aqueous 53% solution, such as those sold by Cognis under the reference Plantacare® 818 UP.

Other examples of nonionic surfactants that may be used in the present disclosure comprise fatty acid alkanolamides (isopropanolamides of fatty acids) such as cocoamide MIPA, lauramide MIPA, Linoleamide MIPA, Myristamide MIPA, Oleamide MIPA, stearamide MIPA, isostearamide MIPA, and mixtures thereof.

Mention may also be made of nonionic surfactants chosen from PEG-40 hydrogented castor oil.

In certain embodiments, the nonionic surfactants of the present disclosure are chosen from (C6-24 alkyl)polyglycosides, and from fatty acid alkanolamides, and more particularly (C8-18 alkyl)(poly)glycosides, ethoxylated C8-C30 fatty acid esters of sorbitan, polyethoxylated C8-C30 fatty alcohols and polyoxyethylenated C8-C30 fatty acid esters, these compounds preferably containing from 2 to 150 mol of ethylene oxide, and mixtures thereof.

In preferred embodiments of the disclosure, the nonionic surfactants are chosen from coco-glucoside, cocamide MIPA, PEG-40 hydrogenated castor oil, and mixtures thereof.

In some embodiments, the nonionic surfactant in the composition of the present disclosure is coco-glucoside. In other embodiments, the nonionic surfactant comprises coco-glucoside and cocamide MIPA.

In various embodiments, when present, the surfactant may be used at a concentration ranging from about 0.01, 0.1, 0.2, 0.3, 0.4, 0.5, 1, 2, 3, 4, 5, 6, 7, 8, 9, 10, 11, 12, 13, 14, 15, 16, 17, 19, 20, 25, 30, 35 or 40 to about 0.5, 1, 2, 3, 4, 5, 6, 7, 8, 9, 10, 11, 12, 13, 14, 15, 16, 17, 19, 20, 25, 30, 35, 40, 45, 50, 55, 60, 65 or 70 wt. %, based on the total weight of the composition.

Solvents

Compositions according to the disclosure comprise a solvent. The solvent may be chosen from water, organic solvents, or mixtures thereof.

In some embodiments, the solvent comprises, consists essentially of, or consists of water. The total amount of water in the compositions may vary depending on the type of composition and the desired consistency, viscosity, etc.

In certain embodiments, the composition comprises, consists essentially of, or consists of non-organic solvents, for example, glycerin, $C_{1-4}$ alcohols, fatty alcohols, fatty ethers, fatty esters, polyols, glycols, vegetable oils, mineral oils, liposomes, laminar lipid materials, or any a mixture thereof. Non-limiting examples of solvents which may be used include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In some cases, the solvent may be selected from the group consisting of one or more glycols, $C_{1-4}$ alcohols, glycerin, and a mixture thereof. For example, the solvent may be selected from the group consisting of hexylene glycol, proplene glycol, caprylyl glycol, glycerin, isopropyl alcohol, or mixtures thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, or mixtures thereof.

Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, or mixtures thereof.

The solvent may be present in the composition in an amount ranging from about 60% to about 98% by weight, relative to the total weight of the composition, including all ranges and subranges therebetween. For example, in one embodiment, the total amount of water may be about 75% to about 98%, about 75% to about 95%, about 75% to 93%, or about 75% to 90% by weight, relative to the total weight of the composition.

Additional Components

The compositions according to the disclosure may also comprise additives chosen from anionic polymers, nonionic polymers, rheoLogy modifiers, thickening and/or viscosity modifying agents, associative or non-associative polymeric thickeners, non-polymeric thickeners, non-polymeric cationic surfactants, nacreous agents, dyes or pigments, fragrances, mineral, plant or synthetic oils, waxes, vitamins, proteins including ceramides, vitamins, UV-screening agents, free-radical scavengers, antidandruff agents, hair-loss counteractants, hair restorers, preserving agents, pH stabilizers and solvents, and mixtures thereof. A person skilled in the art will take care to select the optional additives and the amount thereof such that they do not harm the properties of the compositions of the present disclosure.

If present, these additives are generally present in an amount ranging up to about 40% by weight of active material relative to the total weight of the composition, such as up to about 30%, up to about 20%, up to about 15%, up to about 10%, up to about 5%, such as from 0% to 20%.

The compositions of certain embodiments may comprise stabilizers, for example sodium chloride, magnesium dichloride or magnesium sulfate.

The rheoLogy modifiers and thickening/viscosity-modifying agents that may be employed in compositions of the present disclosure may include any water-soluble or water-dispersible compound that is compatible with the compositions of the disclosure, such as acrylic polymers, non-acrylic polymers, starch, cellulose-based polymers, non-polymeric and polymeric gelling agents, and mixtures thereof.

Methods

Compositions according to the disclosure can be used in methods for removing color from hair, controlling the removal of color from hair, and/or lightening the color of hair. It is to be understood that "removing" color from hair encompasses any degree or kind of color removal. Thus, "removing" color from hair includes removing any amount (e.g. some or all) of color imparted by a particular dye molecule(s) from the hair, or removing any amount (e.g. some or all) of color imparted by one particular dye molecule(s) from the hair regardless of whether any amount of color imparted by another particular dye molecule remains in the hair. Accordingly, it may be possible to completely or substantially remove the color imparted to hair by one or more particular dye molecules, control the removal of color imparted to hair by one or more particular dye molecules, or lighten the color imparted to hair by one or more particular dye molecules through various combinations and amounts of components in the compositions according to the disclosure.

In one or more embodiments, the organic salts may be used to remove color imparted to the hair was imparted by one or more direct dyes which is(are) either hydrophilic (e.g., cationic) or hydrophobic dyes. In various embodiments, the one or more direct dye(s) is(are) hydrophilic. In various embodiments, the one or more direct dye(s) is(are) hydrophobic. In various embodiments, the compositions are particularly useful for removing or controlling the removal of semi-permanent hair color from hair fibers, or lightening the color of hair pre-dyed with semi-permanent hair color.

Methods according to the disclosure comprise contacting a composition according to the disclosure with hair that has been previously dyed, e.g. by one or more direct dyes, optionally leaving the composition on the hair for a period of time, and optionally rinsing the composition from the hair. In preferred embodiments, the composition is rinsed from the hair with water.

In various embodiments, e.g. where the composition is a rinse-off hair treatment or mask or serum, the hair may be massaged with the composition for a period of time and/or the composition may be left on the hair for a period of time ("leave-in time") as desired (e.g., 10, 20, 30 seconds or 1, 2, 3, 4, 5, 6, 7, 8, 9 or 10 minutes to 20, 30 seconds or 1, 2, 3, 4, 5, 6, 7, 8, 9, 10 or 15 minutes). Optionally, the hair may be heated while the composition is in contact with the hair. For example, the hair may be heated at a temperature ranging from about 25° C. to about 60° C., such as with a hair dryer, e.g. a blow dryer or a hood dryer, set at a temperature ranging from about 25° C. to about 60° C. The hair may be subsequently be rinsed.

Without being limited by theory, it is believed that methods according to the disclosure, e.g. contacting hair previously dyed ("pre-dyed hair") with one or more direct dyes with a composition containing an organic salt as described herein, optionally leaving the composition on the hair for a leave-in time, optionally heating the hair, and optionally rinsing the composition from the hair, synergistically improves the ease and speed of removing direct dyes from the hair fibers as compared to merely washing the hair with water.

For example, the compositions described herein may be particularly advantageous for removing azo direct dyes, (poly)methine dyes such as cyanins, hemicyanins and styryls, carbonyl dyes, azine dyes, nitro(hetero)aryl dyes, tri(hetero)arylmethane dyes, porphyrin dyes, phthalocyanin dyes, and natural direct dyes, alone or as mixtures. Without intending to be limited, the following direct dyes are commonly used in semi-permanent hair color, which the compositions according to the disclosure are particularly useful for removing from hair fibers: HC blue 15, hydroxyanthraquinoneaminopropyl methyl morpholinium methosulfate, Basic violet 2, Disperse violet 1, Disperse red 15, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylamino-phenol, Acid red 33, HC violet no. 1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no. 7, Acid red 92, Acid violet 43, Ext violet 2, Acid green 25, or Acid black 1.

Direct Dyes

The methods and compositions of the present disclosure are employed on hair that has been pre-dyed or pre-colored with one or more direct dye(s).

Examples of suitable direct dyes that may be mentioned include azo direct dyes; (poly)methine dyes such as cyanins, hemicyanins and styryls; carbonyl dyes; azine dyes; nitro(hetero)aryl dyes; tri(hetero)arylmethane dyes; porphyrin dyes; phthalocyanin dyes, and natural direct dyes, alone or as mixtures.

Non-limiting examples of direct dyes include nitro dyes which may be chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Nitro dyes include non-ionic direct dyes that are typically hydrophobic. Non-limiting examples of hydrophobic direct dyes may be chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No.

10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15.

In an embodiment, the hydrophobic direct dyes of the present disclosure are chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, and mixtures thereof.

Direct dyes may also be chosen from cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| Het$^+$-C(R$^a$)=N—N(R$^b$)—Ar, An$^-$ | (Va) |
| Het$^+$-N(R$^a$)—N=C(R$^b$)—Ar, An$^-$ | (V'a) |
| Het$^+$—N=N—Ar, An$^-$ | (VIa) |
| An$^+$—N=N—Ar'', An$^-$ | (VI'a) and |
| Het$^+$—N=N—Ar'—N=N—Ar, An$^-$ | (VIIa) | in which formulas (Va), (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more (C$_1$-C$_8$) alkyl groups such as methyl;

Ar$^+$ representing an aryl radical, such as phenyl or naphthyl, bearing an exocyclic cationic charge, preferentially ammonium, particularly tri(C$_1$-C$_8$)alkylammonium such as trimethylammonium;

Ar represents an aryl group, especially phenyl, which is optionally substituted, preferentially with one or more electron-donating groups such as i) optionally substituted (C$_1$-C$_8$)alkyl, ii) optionally substituted (C$_1$-C$_8$) alkoxy, iii) (di)(C$_1$-C$_8$)(alkyl)amino optionally substituted on the alkyl group(s) with a hydroxyl group, iv) aryl(C$_1$-C$_8$)alkylamino, v) optionally substituted N—(C$_1$-C$_8$)alkyl-N-aryl(C$_1$-C$_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups (C$_1$-C$_8$)alkyl, hydroxyl or (C$_1$-C$_8$)alkoxy;

Ar'' is an optionally substituted (hetero)aryl group such as phenyl or pyrazolyl, which are optionally substituted, preferentially with one or more groups (C$_1$-C$_8$)alkyl, hydroxyl, (di)(C$_1$-C$_8$)(alkyl)amino, (C$_1$-C$_8$)alkoxy or phenyl;

R$^a$ and R$^b$, which may be identical or different, represent a hydrogen atom or a group (C$_1$-C$_8$)alkyl, which is optionally substituted, preferentially with a hydroxyl group;

or alternatively the substituent R$^a$ with a substituent of Het$^+$ and/or R$_b$ with a substituent of Ar and/or R$^a$ with R$_b$ form, together with the atoms that bear them, a (hetero)cycloalkyl;

particularly, R$^a$ and R$_b$ represent a hydrogen atom or a group (C$_1$-C$_4$)alkyl, which is optionally substituted with a hydroxyl group; and An$^-$ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

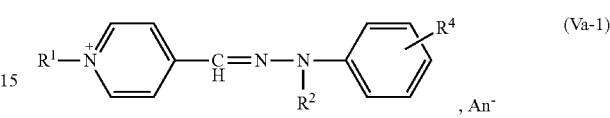

(Va-1)

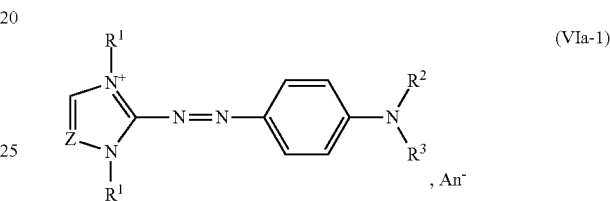

(VIa-1)

wherein in formulae (Va-1) and (VIa-1):

R$^1$ representing a (C$_1$-C$_8$) alkyl group such as methyl;

R$^2$ and R$^3$, which are identical or different, represent a hydrogen atom or a (C$_1$-C$_4$)alkyl group, such as methyl;

R$^4$ represents a hydrogen atom or an electron-donating group such as optionally substituted (C$_1$-C$_8$)alkyl, optionally substituted (C$_1$-C$_8$)alkoxy, or (di)(C$_1$-C$_8$) (alkyl)amino optionally substituted on the alkyl group (s) with a hydroxyl group; particularly, R$^4$ is a hydrogen atom;

Z represents a CH group or a nitrogen atom, preferentially CH; and

An$^-$ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

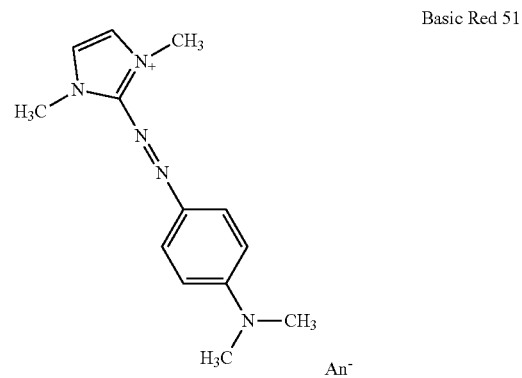

Basic Red 51

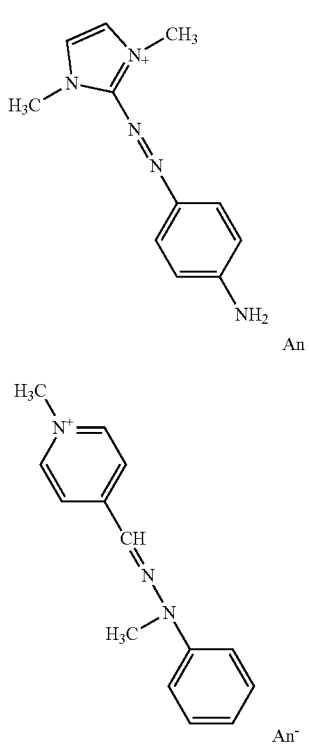

Basic Orange 31

Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic direct dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

In various embodiments, the direct dye used to pre-color or pre-dye the hair according to the present disclosure is selected from non-ionic direct dyes, including hydrophobic direct dyes, ionic direct dyes, including cationic direct dyes and anionic direct dyes, and mixtures thereof.

In various embodiments, the direct dye used to pre-color or pre-dye the hair according to the present disclosure is selected from non-ionic direct dyes, including hydrophobic direct dyes.

In various embodiments, the direct dye used to pre-color or pre-dye the hair according to the present disclosure is selected from ionic direct dyes, including cationic direct dyes and anionic direct dyes, and mixtures thereof. In further embodiments, the direct dye used to pre-color or pre-dye the hair according to the present disclosure is selected from hydrophilic direct dyes.

In various embodiments, the direct dye used to pre-color or pre-dye the hair according to the present disclosure is selected from hydrophobic direct dyes. In other embodiments, the direct dye used to pre-color or pre-dye the hair according to the present disclosure is selected from cationic direct dyes. In yet further embodiments, the direct dye used to pre-color or pre-dye the hair according to the present disclosure comprises a mixture of hydrophobic direct dyes and cationic direct dyes.

In various embodiments, the direct dye used to pre-color or pre-dye the hair according to the present disclosure is selected from the group consisting of HC blue 15, hydroxyanthraquinoneaminopropyl methyl morpholinium methosulfate, Basic violet 2, Disperse violet 1, Disperse red 15, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylaminophenol, Acid red 33, HC violet no. 1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no. 7, Acid red 92, Acid violet 43, Ext violet 2, Acid green 25, Acid black 1 and combinations thereof.

Direct dyes may also be characterized by the partition coefficient (Log $P_{ow}$) values.

$P_{ow}$ is the octanol/water partition coefficient, which can be defined as the ratio of the concentration of a solute, such as the direct dye in the present disclosure, in a water-saturated octanolic phase to its concentration in an octanol-saturated aqueous phase. The octanol/water partition coefficient is typically expressed in Logarithmic form.

There are several existing experimental methods by the Organisation for Economic Co-operation and Development (OECD) and Quantitative Structure-Property Relationship (QSPR) models available for Log Pow measurement or prediction. The experimental methods include: the 'slow-stirring' method (OECD Test No. 123), the high-performance liquid chromatography (HPLC) method (OECD Test No. 117), and shake flask methods (referred to in OECD Test No. 107).

Thus, partition coefficient of a dye may be calculated as follows:

$$\text{Log } P_{ow} = \text{Log } [(\text{dye concentration in octanol})/(\text{dye concentration in water})].$$

The Log $P_{ow}$ value of a direct dye can be positive, negative or neutral. The Log $P_{ow}$ values for some dyes follows in the below table.

| DYE NAMES | Log $P_{ow}$ |
|---|---|
| HC BLUE NO.2 | −0.32 |
| ACID YELLOW 23 | −10.17 |
| BASIC ORANGE 31 | −2.31 |
| BASIC RED 51 | −1.97 |
| BASIC YELLOW 87 | −1.69 |
| ACID YELLOW 3 | −1.05 |
| HC RED NO.3 | −0.42 |
| ACID BLUE 9 | −0.32 |
| BASIC BROWN 17 | −0.15 |
| BASIC YELLOW 57 | 0.06 |
| HC RED NO.7 | 0.13 |
| HC ORANGE NO.2 | 0.13 |

| DYE NAMES | Log $P_{ow}$ |
|---|---|
| 3-NITRO-P-HYDROXYETHYLAMINOPHENOL | 0.21 |
| ACID RED 33 | 0.5 |
| HC VIOLET NO 2 | 0.608 |
| HC VIOLET NO 1 | 0.67 |
| 2-NITRO-5-GLYCERYL METHYLANILINE | 0.89 |
| HYDROXYANTHRAQUINONEAMINO-PROPYL METHYL MORPHOLINIUM METHOSULFATE | 0.89 |
| 3-METHYLAMINO-4-NITROPHENOXYETHANOL | 1.13 |
| 4-AMINO-3-NITROPHENOL | 1.19 |
| HC YELLOW NO.9 | 1.3 |
| ACID RED 52 | 1.3 |
| ACID ORANGE 7 | 1.4 |
| ACID RED18 | 1.63 |
| BASIC BLUE 99 | 1.88 |
| HC BLUE NO.14 | 2.09 |
| HC YELLOW NO.7 | 2.59 |
| DISPERSE VIOLET 1 | 3 |
| ACID RED 92 | 3 |
| ACID VIOLET 43 | 3.1 |
| EXT VIOLET 2 | 3.1 |
| HC BLUE NO. 15 | 3.47 |
| ACID GREEN 25 | 5.71 |
| ACID BLACK 1 | 1.2 |

In one or more embodiments the direct dyes used to dye hair may be characterized by the partition coefficient (Log $P_{ow}$) values, as discussed above.

EXEMPLARY EMBODIMENTS

As discussed above, in some embodiments, the particular uses for the compositions described herein may be tied to the particular organic salt, combination of organic salts, or combination of organic salt and surfactants chosen, as well as to the direct dye that is present on color-treated or pre-dyed hair or on hair dyed with a semi-permanent dye that contains one or more direct dye(s). Thus, the following exemplary embodiments will be provided to help illustrate such combinations, without being limiting.

Exemplary Compositions

In one or more embodiments, the composition of the present disclosure is a hair color remover comprising:

i. about 0.01 to about 50 wt. % of an organic salt selected from:

1. an imidazolium-based compound having a structure represented by Formula (I) below:

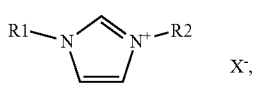

(I)

wherein R1 and R2 are each independently a linear or branched alkyl group having 1-16 carbon atoms, and X– is selected from halides, carboxylates, $C_{1-16}$ fatty acid carboxylates, phosphate, phosphate derivatives, tosylate, tosylate derivatives, sulfate and sulfate derivatives, including alkyl sulfates such as C1-16 sulfates, for example octyl sulfate;

2. an ammonium-based compound having a structure represented by Formula (II) below:

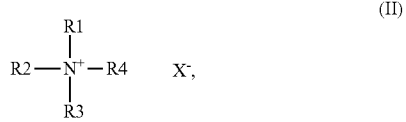

(II)

wherein R1, R2, R3 and R4 are each independently selected from saturated or unsaturated, linear, branched or cyclic groups with the carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and X– is selected from halides, carboxylates, $C_{1-16}$ fatty acid carboxylates, phosphate, phosphate derivatives, tosylate, tosylate derivatives, sulfate and sulfate derivatives; or 3. a combination thereof;

wherein the composition is used for removing one or more direct dye(s) from hair.

In accordance with the present disclosure the above-described compositions are to be used on hair that has been pre-dyed with one or more direct dye(s) which includes, in particular, at least one direct dye having a positive Log $P_{ow}$ value and/or at least one hydrophobic dye, in order to remove from hair at least one direct dye having a positive Log $P_{ow}$ value and/or the at least one hydrophobic dye.

In an embodiment, the one or more direct dyes used to color or pre-dye the hair is HC Blue 15.

In an embodiment, the one or more direct dyes used to color or pre-dye the hair is hydroxyanthraquinoneaminopropyl methyl morpholinium methosulfate.

In an embodiment, the one or more direct dyes used to color or pre-dye the hair is HC Blue 15 and hydroxyanthraquinoneaminopropyl methyl morpholinium methosulfate.

In other embodiments, in accordance with the present disclosure the above-described compositions are to be used on hair that has been pre-dyed with one or more direct dye(s) which includes, in particular, at least one direct dye having a positive Log $P_{ow}$ value (or a hydrophobic direct dye) and at least one direct dye having a negative Log $P_{ow}$ value (or a cationic direct dye).

In an embodiment, the one or more direct dyes used to color or pre-dye the hair is HC Blue 15 and/or Basic Red 51.

Thus, in an embodiment, the disclosure is related to a composition for removing one or more direct dyes from hair, the composition containing:

i. greater than 1 to about 30 wt. % of an organic salt selected from:

1. an imidazolium-based compound having a structure represented by Formula (I) below:

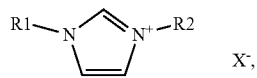

(I)

wherein R1 and R2 are each independently selected from linear and branched alkyl groups having 1-16 carbon atoms, and X– is selected from the group consisting of halides, carboxylates, $C_{1-16}$ fatty acid carboxylates, phosphate, phosphate derivatives, tosylate, tosylate derivatives, sulfate and sulfate derivatives;
2. an ammonium-based compound having a structure represented by Formula (II) below:

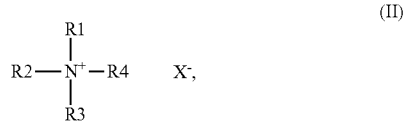

wherein R1, R2, R3 and R4 are each independently selected from saturated or unsaturated, linear, branched or cyclic groups with the carbon chain length of $C_{1-20}$, which are optionally substituted by one or more hydroxyl, amino $C_{1-4}$ radicals, alkylamino, carboxy, carboxylate, carbamide, $C_{1-4}$ alkoxy, —$SO_3H$, sulfonate or aryl; and X– is selected from halides, carboxylates, $C_{1-16}$ fatty acid carboxylates, phosphate, phosphate derivatives, tosylate, tosylate derivatives, sulfate and sulfate derivatives; or
3. a combination thereof; and preferably selected from butyl-3-methylimidazolium octyl sulfate, butyl-3-methylimidazolium acetate, ethyl-3-methylimidazolium ethylsulfate, tributylmethyl ammonium chloride, or combinations thereof; and
ii. optionally, about 0.01 to about 50% wt. % of a surfactant selected from an anionic surfactant, a nonionic surfactant, an amphoteric surfactant and combinations thereof;
wherein the one or more direct dye(s) includes at least one hydrophobic dye and/or at least one direct dye having a positive Log $P_{ow}$ value;
wherein all weights are based on the total weight of the composition.
Exemplary Methods In various embodiments, the disclosure is directed to methods of contacting hair with the compositions described herein in order to remove, from pre-dyed hair, one or more direct dyes comprising at least one hydrophobic dye and/or at least one direct dye having a positive Log $P_{ow}$ value. Furthermore, the present disclosure is directed to methods of contacting hair with the compositions described herein in order to remove color or lighten the color of hair that has been colored or pre-dyed with a hair dye containing one or more direct dyes comprising at least one hydrophobic dye and/or at least one direct dye having a positive Log $P_{ow}$ value. The one or more direct dyes can further comprise ionic direct dyes, such as for example cationic or hydrophilic direct dyes and/or direct dye having a negative Log $P_{ow}$ value, or nonionic direct dyes having a neutral Log $P_{ow}$ value.

Without wishing to be bound to any one theory, it is believed that the ionicitities of the direct dyes and/or the types and/or amounts of organic salt and surfactants can be utilized to control the degree and/or speed of removal of direct dyes or removal/lightening of color from pre-dyed hair.

In non-limiting exemplary embodiments, composition according to the disclosure may be combined with other another composition, e.g. a rinse-off hair shampoo or conditioner or mask. In such embodiments, the methods would include those steps customary in using shampoos and/or conditioners and/or rinse-off masks or treatments. For example, the hair may be massaged with the composition for a period of time and/or the composition may be left on the hair for a period of time ("leave-in time") as desired (e.g., 10, 20, 30 seconds or 1, 2, 3, 4, 5, 6, 7, 8, 9 or 10 minutes to 20, 30 seconds or 1, 2, 3, 4, 5, 6, 7, 8, 9, 10 or 15 minutes), and optionally heated. The hair is then rinsed after each treatment.

Examples

The ingredient amounts in the composition/formulations described below are expressed in % by weight, based on the total weight of the composition, unless otherwise indicated.

Several organic salts were tested for efficacy for color removal of several direct dyes. The organic salts tested are indicated in the table below.

| Organic Salts Tested | |
|---|---|
| Name | Structure |
| Butyl-3-methylimidazolium octyl sulfate (BMIM octyl sulfate) | |
| Butyl-3-methylimidazolium acetate (BMIM OAc) | |
| Ethyl-3-methylimidazolium ethylsulfate (EMIM ethylsulfate) | |
| Tributylmethyl ammonium chloride (TBuMA Cl) | |

Unless otherwise indicated, the formulations described contained the active ingredients listed with the balance made up of water.

Unless otherwise indicated, hair swatches were all treated using the same protocol. Specifically, 2 g dyed hair swatches are soaked in 80 g treatment solution in water for 30 minutes at 40° C., then the treated hair swatches are then shampooed/washed once (rinsing step) and blow-dried for evaluation.

Unless otherwise indicated, color removal performance is measured using CIE L* a* b* coordinates. ΔE is used to describe the color difference and is defined by the following equation:

$$\Delta E^*_{ab} = \sqrt{(L^*_2 - L^*_1)^2 + (a^*_2 - a^*_1)^2 + (b^*_2 - b^*_1)^2}$$

where, $L_1*$, $a_1$; $b_1$ are measured on freshly dyed hair $L_2*$, $a_2$, $b_2$ are measured on the dyed hair treated by color remover systems. The higher ΔE values, the more efficient the color removal.

Example 1—Removal of HC Blue 15 Using Organic Salts

HC Blue 15 contains multi-aromatic rings and has the structure below. The Log $P_{ow}$ value around 3.47.

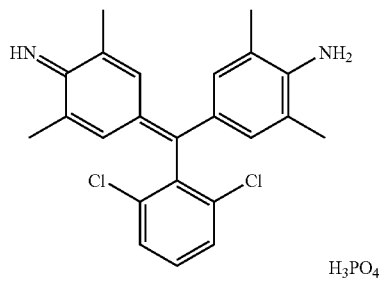

Hair swatches dyed with HC Blue 15 were treated with the organic salts at varying concentrations using the protocol described above. The resulting ΔE are shown in the below table, as well as in FIG. 1.

ΔE Values

| Concentration of Organic salt | BMIM Octyl sulfate | BMIM OAc | TBuMA Cl | EMIM ethylsulfate |
|---|---|---|---|---|
| 0% (control) | 6.0 | | | |
| 1% | 1.3 | 3.6 | | 1.1 |
| 5% | 18.4 | 1.1 | | 2.1 |
| 10% | 32.2 | 5.6 | 1.8 | 1.5 |
| 25% | | 8.6 | 32.8 | 9.3 |
| 50% | | 36.14 | | 26.8 |

As seen from the FIG. 1, the organic salts are capable of enhancing the removal of dye. Starting at about 5% of the organic salt, the ΔE value increased significantly for BMIM octyl sulfate, indicating significant removal of the dye. For the other organic salts, a significant increase in the ΔE values was observed starting at about 25% of the organic salt. Thus, more color, i.e., a greater amount of dye is removed as the concentration of the organic salt was increased. Moreover, the significantly higher ΔE values after treatment of the hair with organic salt solutions were accompanied by removal of color from or lightening of the color of the hair as visually seen by the naked eye.

Example 2—Removal of Basic Red 51

Hair swatches dyed with Basic Red 51 were treated with BMIM octylsulfate and TBuMA Cl, each at 10% concentration using the protocol described above. Basic Red 51 contains a quaternary moiety and has the structure below. The Log $P_{ow}$ value around −1.97.

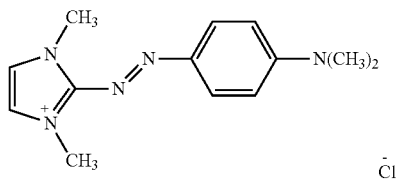

Figure 2:
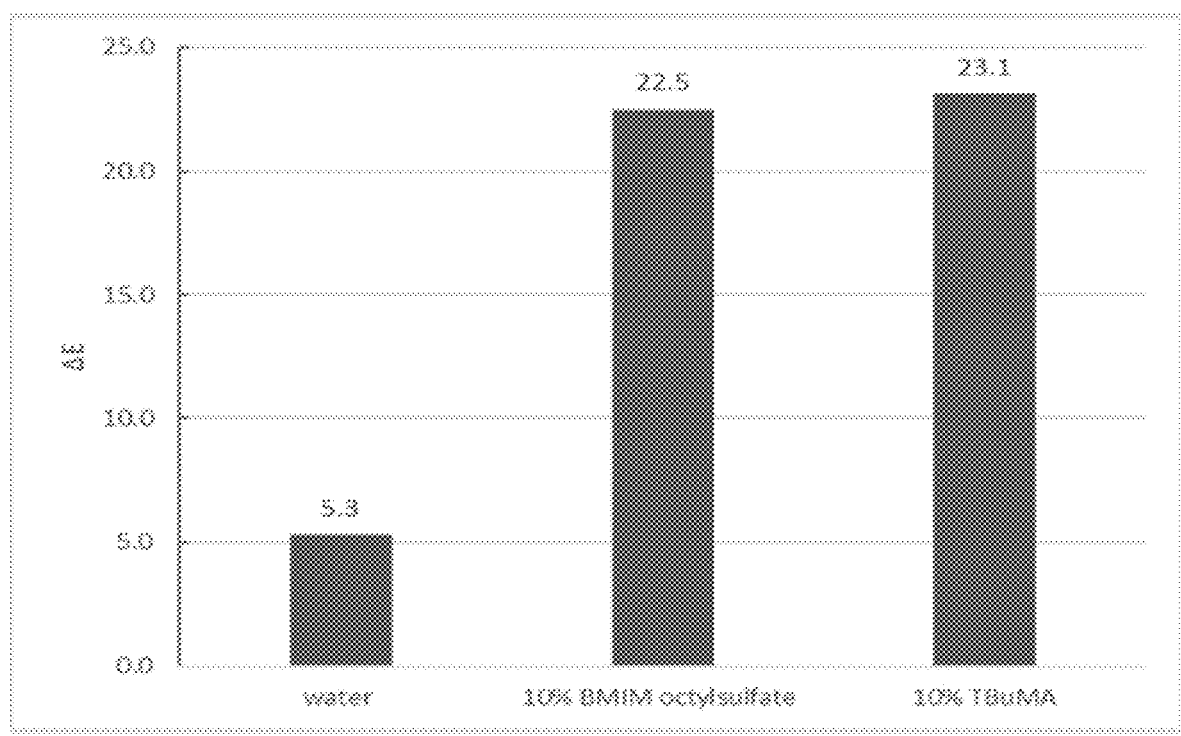
FIG. 2 is a graphical representation of ΔE values of dyed hair swatches treated with water and two solutions, each containing a different organic salt.

The resulting ΔE are in FIG. 2. For the treatment with water alone (control), the ΔE value was 5.3. For the treatment with BMIM octyl sulfate, the ΔE value was 22.2 and for the treatment with TBuMA Cl, the ΔE value was 23.1. As shown by the results, BMIM octylsulfate and TBuMA Cl can remove Basic Red 51 from hair fibers.

Example 3—Removal of Hydroxyanthraquinoneaminopropyl Methyl Morpholinium Methosulfate Hair swatches dyed with hydroxyanthraquinoneaminopropyl methyl morpholinium methosulfate were treated with BMIM octylsulfate at 10% concentration using the protocol described above. Hydroxyanthraquinoneaminopropyl methyl morpholinium methosulfate has the structure below, and a Log $P_{ow}$ value around 2.89.

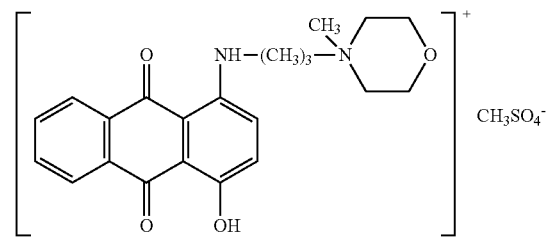

Figure 3:
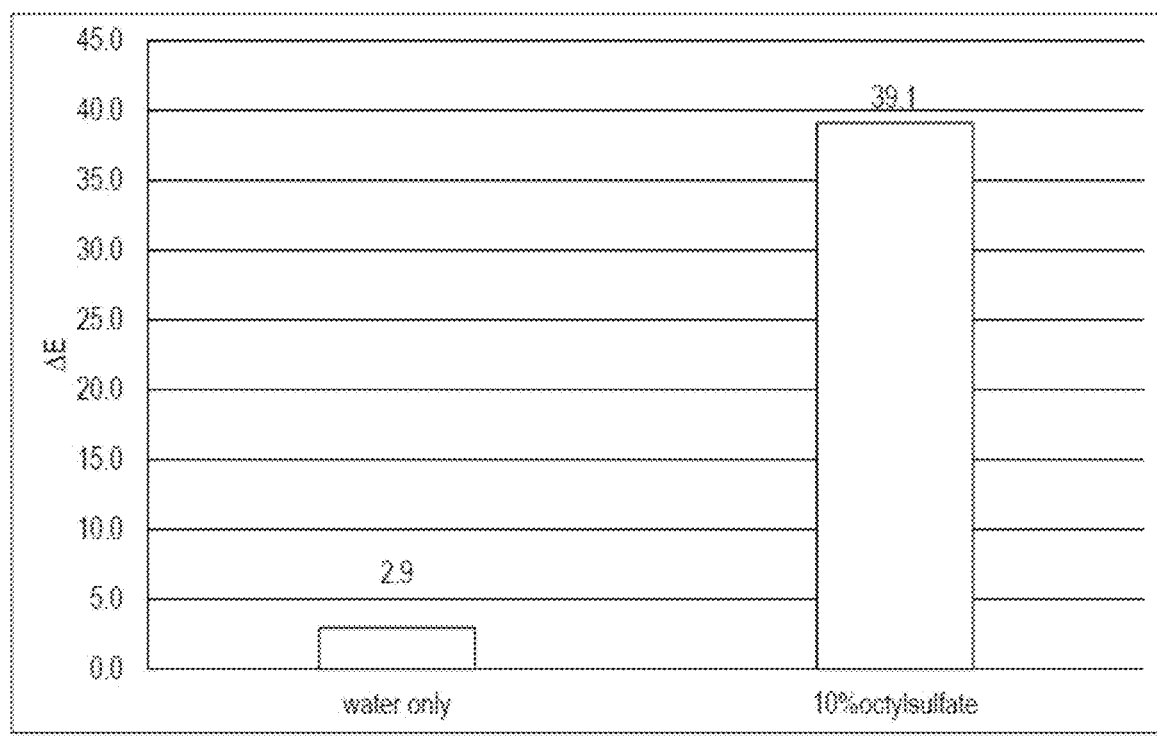
FIG. 3 is a graphical representation of ΔE values of dyed hair swatches treated with water and a solution containing an organic salt.

The resulting ΔE values are in FIG. 3. For the treatment with water alone (control), the ΔE value was 2.9. For the treatment with BMIM octyl sulfate, the ΔE value was 39.1. As shown by the results, BMIM octylsulfate can remove hydroxyanthraquinoneaminopropyl methyl morpholinium methosulfate from hair fibers.

The terms "comprising," "having," and "including" are used in their open, non-limiting sense.

The terms "a" and "the" are understood to encompass the plural as well as the singular.

The compositions and methods of the present disclosure can comprise, consist of, or consist essentially of the essential elements and limitations of the disclosure described herein, as well as any additional or optional ingredients, components, or limitations described herein or otherwise useful.

All percentages, parts and ratios herein are based upon the total weight of the compositions of the present disclosure, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

Other than in the operating examples, or where otherwise indicated, all numbers expressing quantities of ingredients and/or reaction conditions are to be understood as being modified in all instances by the term "about" which can encompass +/−10%, +/−8%, +/−6%, +/−5%, +/−4%, +/−3%, +/−2%, +/−1%, or +/−0.5%.

All numbers expressing pH values are to be understood as being modified in all instances by the term "about" which encompasses up to +/−3%. As used herein, the expression "at least one" is interchangeable with the expression "one or more" and thus includes individual components as well as mixtures/combinations.

The term "active material" as used herein with respect to the percent amount of an ingredient or raw material, refers to 100% activity of the ingredient or raw material.

The terms "a," "an," and "the" are understood to encompass the plural as well as the singular. Thus, the term "a mixture thereof" also relates to "mixtures thereof.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, haLogen containing groups, ester groups, thiol groups, sulphonate groups, thiosulphate groups, siloxane groups, and polysiloxane groups. The substituent(s) may be further substituted.

The term "neutralized" as used herein is intended to mean that the 3-butoxypropylamine is protonated with a $H_+$ (proton) coming from the diacid(s).

The term "substantially free of (a component)" as defined herein means that the system or composition contains no appreciable amount of the component, for example, no more than about 1% by weight, no more than about 0.5% by weight, or no more than about 0.3% by weight, such as no more than about 0.1% by weight, based on the weight of the composition.

The term "free" or "completely free of (a component)" as defined herein means that the composition does not contain the component in any measurable degree by standard means.

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counter-ion. This list of counter-ions, however, is non-limiting.

The expression "inclusive" for a range of concentrations means that the limits of the range are included in the defined interval.

All components and elements positively set forth in this disclosure can be negatively excluded from the claims. In other words, the compositions of the instant disclosure can be free or essentially free of all components and elements positively recited throughout the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A method for removing one or more direct dyes from hair, the method comprising:
   a. contacting the hair with a composition comprising:
      i. at least one organic salt chosen from:
         an imidazolium-based compound of Formula (I):

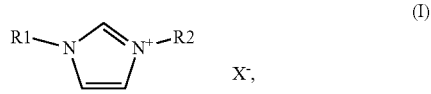

wherein
         R1 and R2 are each independently a linear or branched alkyl group having 1-16 carbon atoms, and
         $X^-$ is chosen from halides, carboxylates, C1-16 fatty acid carboxylates, phosphates, phosphate derivatives, tosylates, tosylate derivatives, sulfates, or sulfate derivatives;
      an ammonium-based compound of Formula (II):

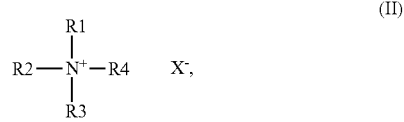

wherein
         R1, R2, R3 and R4 are each independently a saturated or unsaturated, linear, branched or cyclic group with a carbon chain length of $C_{1-20}$, optionally substituted with one or more hydroxyl, amino $C_{1-4}$ radicals, alkylamino, carboxy, carboxylate, carbamide, $C_{1-4}$ alkoxy, —$SO_3H$, sulfonate or aryl; and
         $X^-$ is chosen from halides, carboxylates, C1-16 fatty acid carboxylates, phosphates, phosphate derivatives, tosylates, tosylate derivatives, sulfates, or sulfate derivatives; or
      combinations thereof; and
   b. rinsing the composition from the hair.

2. The method of claim 1, wherein:
   R1, R2, R3, and R4 of Formula (II) are each independently a linear or branched alkyl group with a carbon chain length of $C_{1-20}$; and
   $X^-$ of Formula (II) is chosen from carboxylates, $C_{1-16}$ fatty acid carboxylates, sulfates, or sulfate derivatives, including alkyl sulfates.

3. The method of claim 1, wherein the compound of Formula (II) is chosen from:

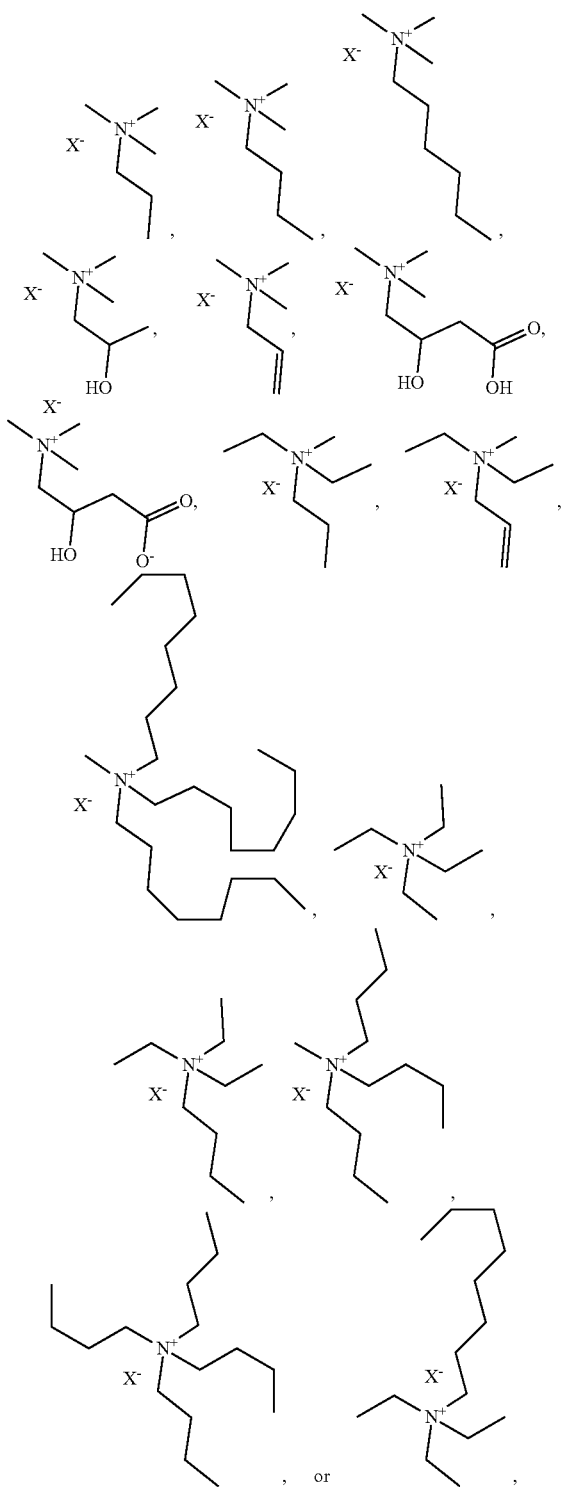

wherein X⁻ is chosen from halides, carboxylates, $C_{1-16}$ fatty acid carboxylates, phosphates, phosphate derivatives, tosylates, tosylate derivatives, sulfates, or sulfate derivatives.

4. The method of claim 1, wherein the at least one organic salt is chosen from 1-butyl-3-methylimidazolium octyl sulfate, 1-butyl-3-methylimidazolium acetate, 1-ethyl-3-methylimidazolium ethylsulfate, 1-ethyl-3-ethyl imidazolium acetate, 1-ethyl-3-methylimidazolium tosylate, or combinations thereof.

5. The method of claim 1, wherein the at least one organic salt is chosen from an ammonium-based compound comprising a tributylmethyl ammonium salt.

6. The method of claim 1, wherein the at least one organic salt is chosen from an imidazolium-based compound of Formula (I) in ionic liquid form.

7. The method of claim 1, wherein the at least one organic salt is chosen from an ammonium-based compound of Formula (II) in ionic liquid form.

8. The method of claim 1, wherein the at least one organic salt is present in the composition at a concentration of greater than about 1% by weight, based on the total weight of the composition.

9. The method of claim 1, wherein the composition further comprises a surfactant.

10. The method of claim 1, wherein the one or more direct dyes is chosen from:
    direct dyes having a positive Log $P_{ow}$ value,
    direct dyes having a negative Log $P_{ow}$ value,
    direct dyes having a neutral Log $P_{ow}$ value, or
    combinations thereof.

11. The method of claim 10, wherein the direct dyes having a positive Log $P_{ow}$ value are chosen from hydrophobic direct dyes including HC blue 15, hydroxyanthraquinoneaminopropyl methyl morpholinium methosulfate, Basic violet 2, Disperse violet 1, Disperse red 15, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylaminophenol, Acid red 33, HC violet no. 1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no. 7, Acid red 92, Acid violet 43, Ext violet 2, Acid green 25, Acid black 1, or combinations thereof.

12. The method of claim 10, wherein the direct dyes having a negative Log $P_{ow}$ value are chosen from cationic direct dyes including basic orange 31, basic red 51, basic yellow 57, HC blue no. 2, Acid yellow 23, Basic orange 31, Basic yellow 87, Acid yellow 3, HC Red 3, Acid blue 9, Basic brown 17, or combinations thereof.

13. The method of claim 1, wherein one or more direct dyes is removed from the hair or the hair is lightened following step (b).

14. The method of claim 1, wherein:
    the one or more direct dyes is chosen from direct dyes having a positive Log $P_{ow}$ value, and
    the organic salt is chosen from:
        an imidazolium-based compound chosen from butyl-3-methylimidazolium octyl sulfate, butyl-3-methylimidazolium acetate, ethyl-3-methylimidazolium ethylsulfate, 1-ethyl-3-ethyl imidazolium acetate, or 1-ethyl-3-methylimidazolium tosylate,
        tributylmethyl ammonium chloride, or
        combinations thereof.

15. The method of claim 1, wherein:
    the one or more direct dyes is chosen from direct dyes having a negative Log $P_{ow}$ value, and
    the organic salt is chosen from 1-butyl-3-methylimidazolium octyl sulfate, tributylmethyl ammonium chloride, or a combination thereof.

16. A method for removing color from hair, controlling the removal of color from hair, or lightening the color of hair, the method comprising:
a. contacting the hair with a composition comprising:
  i. at least one organic salt chosen from:
    an imidazolium-based compound of Formula (I):

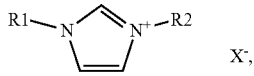

wherein
  R1 and R2 are each independently a linear or branched alkyl group having 1-16 carbon atoms, and
  X⁻ is chosen from halides, carboxylates, C1-16 fatty acid carboxylates, phosphates, phosphate derivatives, tosylates, tosylate derivatives, sulfates, or sulfate derivatives;
  an ammonium-based compound of Formula (II):

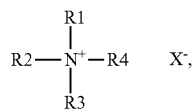

wherein
  R1, R2, R3 and R4 are each independently a saturated or unsaturated, linear, branched or cyclic group with a carbon chain length of $C_{1-20}$, optionally substituted with one or more hydroxyl, amino $C_{1-4}$ radicals, alkylamino, carboxy, carboxylate, carbamide, $C_{1-4}$alkoxy, —SO₃H, sulfonate, or aryl; and
  X⁻ is chosen from halides, carboxylates, $C_{1-16}$ fatty acid carboxylates, phosphates, phosphate derivatives, tosylates, tosylate derivatives, sulfates, or sulfate derivatives; or
  combinations thereof; and
b. rinsing the composition from the hair;
  wherein the hair has been pre-dyed with one or more direct dyes.

17. The method of claim 16, wherein R1, R2, R3, and R4 of Formula (II) are each independently a linear or branched alkyl group with a carbon chain length of $C_{1-20}$, and X⁻ of Formula (II) is chosen from carboxylates, $C_{1-16}$ fatty acid carboxylates, sulfates, or sulfate derivatives, including alkyl sulfates.

18. The method of claim 16, wherein the ammonium-based compound of Formula (II) is chosen from:

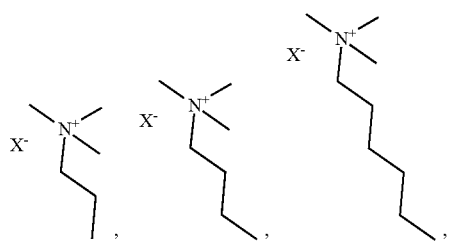
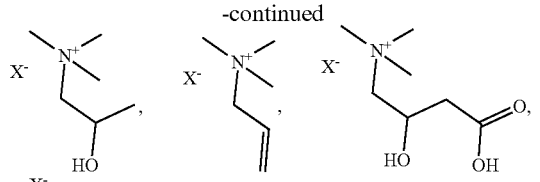
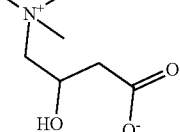
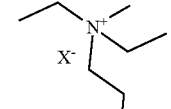
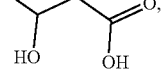
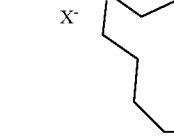
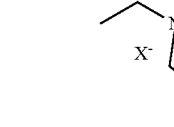
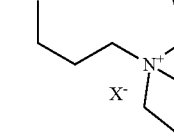
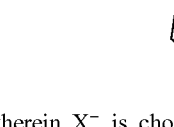
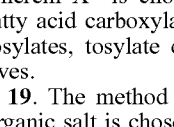
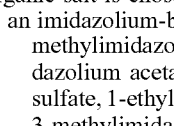
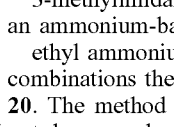
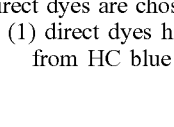

wherein X⁻ is chosen from halides, carboxylates, C1-16 fatty acid carboxylates, phosphates, phosphate derivatives, tosylates, tosylate derivatives, sulfates, or sulfate derivatives.

19. The method of claim 16, wherein the at least one organic salt is chosen from:
  an imidazolium-based compound chosen from 1-butyl-3-methylimidazolium octyl sulfate, 1-butyl-3-methylimidazolium acetate, 1-ethyl-3-methylimidazolium ethylsulfate, 1-ethyl-3-ethyl imidazolium acetate, or 1-ethyl-3-methylimidazolium tosylate;
  an ammonium-based compound chosen from tributylmethyl ammonium salts; or
  combinations thereof.

20. The method of claim 16, wherein the one or more direct dyes are chosen from:
  (1) direct dyes having a positive Log $P_{ow}$ value chosen from HC blue 15, hydroxyanthraquinoneaminopropyl methyl morpholinium methosulfate, Basic violet 2, Disperse violet 1, Disperse red 15, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylaminophenol, Acid red 33, HC violet no. 1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no. 7, Acid red 92, Acid violet 43, Ext violet 2, Acid green 25, Acid black 1; or (2) direct dyes having a negative Log $P_{ow}$ value chosen from basic orange 31, basic red 51, basic yellow 57, HC blue no. 2, Acid yellow 23, Basic orange 31, Basic yellow 87, Acid yellow 3, HC Red 3, Acid blue 9, Basic brown 17; or (3) combinations thereof.

21. A composition for removing one or more direct dyes from hair, the composition comprising at least one organic salt chosen from:

an imidazolium-based compound chosen from 1-butyl-3-methylimidazolium octyl sulfate, 1-butyl-3-methylimidazolium acetate, 1-ethyl-3-methylimidazolium ethylsulfate, 1-ethyl-3-ethyl imidazolium acetate, or 1-ethyl-3-methylimidazolium tosylate;

an ammonium-based compound chosen from tributylmethyl ammonium salts; or combinations thereof;

wherein the at least one organic salt is present in the composition at a concentration effective to remove one or more direct dyes from the hair, based on the total weight of the composition.

22. The composition of claim 21, wherein the one or more direct dyes is chosen from:

(1) direct dyes having a positive Log $P_{ow}$ value chosen from HC blue 15, hydroxyanthraquinoneaminopropyl methyl morpholinium methosulfate, Basic violet 2, Disperse violet 1, Disperse red 15, Disperse blue 3, Disperse blue 377, Disperse 99, Solvent violet 13, Basic blue 6, HC blue 16, Basic blue 99, HC blue 14, Basic brown 16, Acid green 25, Acid black 1, HC red 7, HC orange 2, 3-Nitro-p-hydroxyethylaminophenol, Acid red 33, HC violet no. 1, 2-Nitro-5-glyceryl methylaniline, 3-Methylamino-4-nitrophenoxyethanol, 4-Amino-3-nitrophenol, H yellow 9, Acid red 52, Acid orange 7, Acid red 18, HC yellow no. 7, Acid red 92, Acid violet 43, Ext violet 2, Acid green 25, or Acid black 1;

(2) direct dyes having a negative Log $P_{ow}$ value chosen from basic orange 31, basic red 51, basic yellow 57, HC blue no. 2, Acid yellow 23, Basic orange 31, Basic yellow 87, Acid yellow 3, HC Red 3, Acid blue 9, or Basic brown 17; or (3) combinations thereof.

* * * * *